(12) United States Patent
Neuman et al.

(10) Patent No.: US 10,995,004 B2
(45) Date of Patent: May 4, 2021

(54) METHOD FOR FUNCTIONALIZING CARBON NANOPARTICLES AND COMPOSITIONS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Keir Cajal Neuman, Bethesda, MD (US); Ganesh Shenoy, Danville, PA (US); Chandrasekhar Mushti, Bethesda, MD (US); Rolf E. Swenson, Bethesda, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 262 days.

(21) Appl. No.: 16/336,709

(22) PCT Filed: Sep. 29, 2017

(86) PCT No.: PCT/US2017/054351
§ 371 (c)(1),
(2) Date: Mar. 26, 2019

(87) PCT Pub. No.: WO2018/064504
PCT Pub. Date: Apr. 5, 2018

(65) Prior Publication Data
US 2020/0207627 A1     Jul. 2, 2020

Related U.S. Application Data

(60) Provisional application No. 62/402,339, filed on Sep. 30, 2016.

(51) Int. Cl.
| | |
|---|---|
| *C01B 32/28* | (2017.01) |
| *C07C 51/347* | (2006.01) |
| *C07C 59/125* | (2006.01) |
| *C07C 231/12* | (2006.01) |
| *C07C 235/08* | (2006.01) |
| *C07C 327/30* | (2006.01) |
| *C07D 207/448* | (2006.01) |
| *C07D 225/08* | (2006.01) |
| *C07D 239/47* | (2006.01) |
| *C07D 473/18* | (2006.01) |
| *B82Y 30/00* | (2011.01) |
| *B82Y 40/00* | (2011.01) |

(52) U.S. Cl.
CPC ............ *C01B 32/28* (2017.08); *C07C 51/347* (2013.01); *C07C 59/125* (2013.01); *C07C 231/12* (2013.01); *C07C 235/08* (2013.01); *C07C 327/30* (2013.01); *C07D 207/448* (2013.01); *C07D 225/08* (2013.01); *C07D 239/47* (2013.01); *C07D 473/18* (2013.01); *B82Y 30/00* (2013.01); *B82Y 40/00* (2013.01); *C01P 2002/82* (2013.01); *C01P 2004/64* (2013.01)

(58) Field of Classification Search
CPC ....... C01B 32/28; C01B 32/00; C07C 51/347; C07C 59/125; C07C 231/12; C07C 235/08; C07C 327/30; C07D 207/448; C07D 225/08; C07D 239/47; C07D 473/18; B82Y 30/00; B82Y 40/00; C01P 2002/82; C01P 2004/64
See application file for complete search history.

(56) References Cited

U.S. PATENT DOCUMENTS

| | | |
|---|---|---|
| 2010/0298600 A1 | 11/2010 | Lee |
| 2012/0116094 A1 | 5/2012 | Swager et al. |
| 2014/0314850 A1 | 10/2014 | Badea et al. |
| 2016/0068398 A1 | 3/2016 | Myllymaki et al. |

OTHER PUBLICATIONS

Mochalin, et al., The properties and applications of nanodiamonds, Nature Nanotechnology 2012; 7: 11-23 (Year: 2012).*
Rogel-Hernandez, et al., Side-Wall Functionalization of Multi-Walled Carbon Nanotubes with t-Butyl Diazoacetate, J. Mex. Chem. Soc. 2011; 55(1): 7-10 (Year: 2011).*
Naeimi, et al., Efficient and facile one pot carboxylation of multiwalled carbon nanotubes by using oxidation with ozone under mild conditions, Applied Surface Science 2009; 256: 631-635 (Year: 2009).*
Aller, Enrique, et al., "Diastereoselectivity in the O—H Insertion Reactions of Rhodium Carbenoids Derived from Phenyldiazoacetates of Chiral Alcohols. Preparation of a-Hydroxy and a-Alkoxy Esters" J. Org. Chem. 1995, 60, pp. 4449-4460.
Chang, Be-Ming et al.,"Highly Fluorescent Nanodiamonds Protein-Functionalized for Cell Labeling and Targeing", Adv. Funct. Mater. 2013, 23(46), pp. 5737-5745.
Fu, Chi-Cheng et al., "Characterization and application of single fluorescent nanodiamonds as cellular biomarkers", PNAS, Jan. 16, 2007, vol. 104, No. 3; pp. 727-732.

(Continued)

*Primary Examiner* — Daniel C. McCracken
(74) *Attorney, Agent, or Firm* — Cantor Colburn LLP

(57) ABSTRACT

A method of increasing a density of carboxylic acids on a surface of a carbon nanoparticle is disclosed. The method includes contacting an oxygen-containing functional group on a surface of a carbon nanoparticle with a reducing agent to provide a hydroxyl group; reacting the hydroxyl group with a diazoacetate ester in the presence of a transition metal catalyst to provide an ester, the diazoacetate ester having the structure wherein R is a C1-8 hydrocarbyl, preferably tert-butyl, methyl, ethyl, isopropyl, allyl, benzyl, pentafluorophenyl, or N-succinimidyl; and cleaving the ester to provide a carboxylic acid group. Surface-functionalized carbon nanoparticles made by the method are also disclosed.

20 Claims, 5 Drawing Sheets

(56) References Cited

OTHER PUBLICATIONS

Hoehnel, S. and Lutolf, M.P., "Capturing Cell-Cell Interactions via SNAP-tag and CLIP-tag Technology", Bioconjugate Chem. 2015, 26, pp. 1678-1686.

Huang, Jie et al., "Chemical analysis of surface oxygenated moieties of fluorescent carbon nanoparticles", Nanoscale, 2012, 4; p. 1010-1015.

International Search Report for International Application No. PCT/2017/054351; International Filing date: Sep. 29, 2017; dated Dec. 20, 2017; 6 pages.

Isaacs, L. et al., "Improved purification of C60 and formation of sigma- and pi-Hooaromatic Methano-Bridged Fullerenes by Reaction with Alkly Diazoacetate", Helv. Chim. Acta 1993, 76, 1231-1250.

Mochalin, Vadym N., et al., The properties and applications of nanodiamonds, Nature Nanotechnology, vol. 7, Jan. 2012; pp. 11-23.

Moon, Woo Kyung, et al., "Enhanced Tumor Detection Using a Folate Receptor-Targeted Near-infrared Fluorochrome Conjugate", Bioconjugate Chem., 2003, 14, pp. 539-545.

Nystrom, R.F. et al., "Reduction of Organic Compounds by Lithium Aluminum Hydride. I., Aldehydes, Ketones, Esters, Acid Chlorides and Acid Anhydrides", Journal of the American Chemical Society, May 1947, 69 (5); pp. 1197-1199.

Nystrom, R.F. et al., "Reduction of Organic Compounds by Lithium Aluminum Hydride. II Carboxylic Acids", Journal of the American Chemical Society, 1947, 69 (10), pp. 2548-2549.

Rogel-Hernandez, Eduardo et al., "Side-wall Functionalization of Multi-Walled Carbon Nanotubes with t-Butyl Diazoacetate", J. Mex. Chem. Soc., 2011, 55 (1) pp. 7-10.

Written Opinion of the International Searching Authority for International Application No. PCT/2017/054351; International Filing date: Sep. 29, 2017; dated Dec. 20, 2017; 9 pages.

\* cited by examiner

METHOD FOR FUNCTIONALIZING CARBON NANOPARTICLES AND COMPOSITIONS

STATEMENT OF GOVERNMENT SUPPORT

This invention was made in part with government support from the National Institutes of Health. The government has certain rights in this invention.

BACKGROUND

Carboxylic acids are one of the most commonly utilized functional groups for covalent surface conjugation of nanoparticles. For example, for biological or biomedical applications, carboxylic acids are one of the most useful functional groups as a result of their utility in coupling with biologically relevant molecules such as antibodies and other peptides.

Currently, the most common method to produce carboxylic acids on carbon nanoparticle surfaces is through treatment with an oxidizing acid mixture, for example nitric or sulfuric acid. Subjecting carbon nanoparticles to such oxidizing environments results in the formation of many oxygen-containing functional groups on the nanoparticle surface. The functional groups produced include epoxides, ketones, aldehydes, carboxylic acids, and lactones. (See, Mochalin, V. N.; Shenderova, O.; Ho, D.; Gogotsi, Y., The Properties and Applications of Nanodiamonds. *Nature Nanotechnology* 2012, 7 (1), 11-23; Huang, J.; Deming, C. P.; Song, Y.; Kang, X.; Zhou, Z.-Y.; Chen, S., Chemical Analysis of Surface Oxygenated Moieties of Fluorescent Carbon Nanoparticles. *Nanoscale* 2012, 4 (3), 1010-1015.) Unfortunately, it is difficult to selectively produce carboxylic acids using this acid treatment technique. This presents several problems, one being that a product with a mixture of functional groups is less likely to be used for therapeutic purposes as a result of unintended reactions and poor characterization. Additionally, having the total oxygen content on the nanoparticle surface present in many different forms results in a lower total carboxylic acid content and subsequently lower loading of the molecules that later become coupled to the carboxylic acids.

During ongoing development of fluorescent nanodiamonds (FNDs) as molecular imaging probes, the inventors have repeatedly encountered the problem of low carboxylic acid content, which prevents the functionalization of the FNDs essential for most applications. Other researchers and the manufacturers of the diamonds have reported low to no yield when using carboxylic acid-based coupling approaches for FNDs. The low abundance of carboxylic acid groups on the FNDs thus represents a significant barrier to efficient and biologically compatible functionalization, and more generally the functionalization of other carbon nanoparticles.

Thus, there is a need for improved methods of increasing the density of carboxylic acids on a carbon nanoparticle surface.

SUMMARY

Disclosed herein are methods of increasing the density of carboxylic acids on a surface of a carbon nanoparticle. The method includes contacting an oxygen-containing functional group on a surface of a carbon nanoparticle with a reducing agent to provide a hydroxyl group; reacting the hydroxyl group with a diazoacetate ester in the presence of a transition metal catalyst to provide an ester, and cleaving the ester to provide a carboxylic acid group.

A surface-functionalized carbon nanoparticle including carboxylic acid groups is also disclosed.

In an embodiment, the surface-functionalized carbon nanoparticle includes a first functional group attached to a surface of the carbon nanoparticle, wherein the first functional group is present in an amount of at least $3\times10^{17}$ first functional group/gram (g) of 80 nm diameter carbon nanoparticles, at least 300 first functional groups/carbon nanoparticle, or at least 1 first functional group per 70 $nm^2$ of the surface of the carbon nanoparticle.

These and other advantages, as well as additional inventive features, will be apparent from the following Drawings, Detailed Description, Examples, and Claims.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
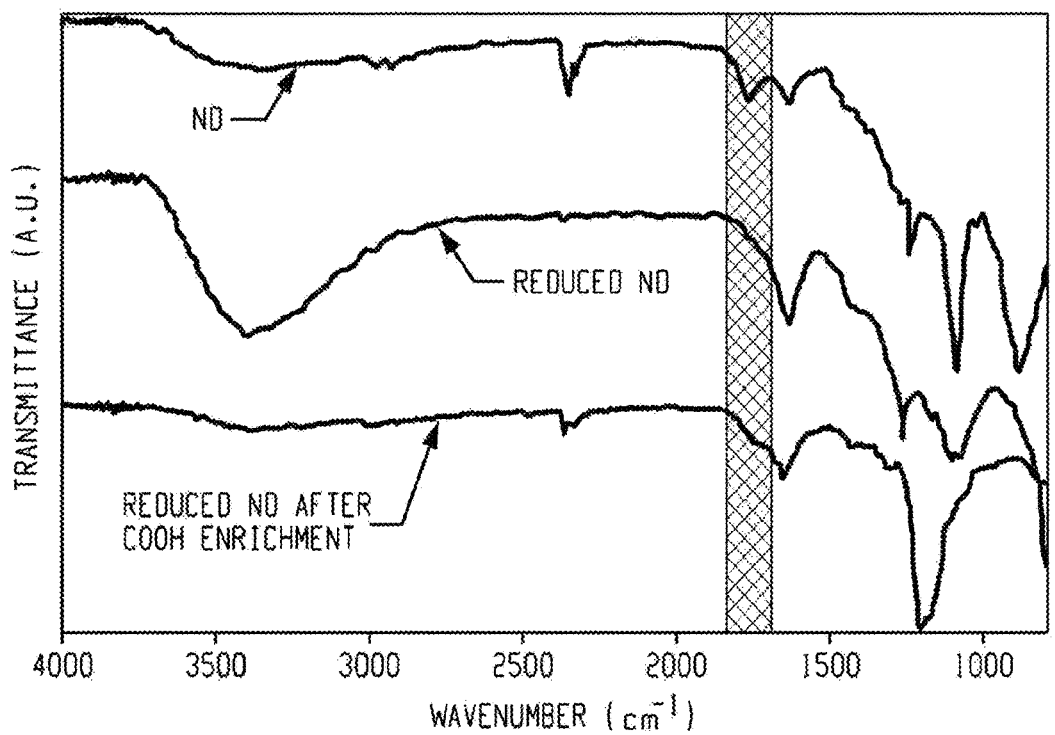
FIG. 1 presents infrared (IR) spectra of detonation nanodiamonds through the carboxylic acid enrichment procedure. The spectra correspond to untreated detonation nanodiamonds (top spectrum), nanodiamonds reduced with $LiAlH_4$ (LAH) (middle spectrum), and LAH-reduced diamonds following carbenoid insertion reaction and subsequent ester cleavage (bottom spectrum). The vertical grey region at ~1750 $cm^{-1}$ highlights the C=O stretch region.

Carbon nanomaterials such as fluorescent nanodiamonds, graphene, and single- or multi-walled carbon nanotubes can have significant biological applications in the near future. Carboxylic acids are one of the most useful functional groups in biological chemistry as a result of their utility in coupling with biologically relevant molecules, such as antibodies and other peptides. Currently, the most common way of producing carboxylic acids on carbon nanoparticle surfaces is through treatment with an oxidizing acid mixture, typically nitric and sulfuric acid. However, treating carbon nanoparticles with oxidizing acids generates a wide mixture of oxygen-containing functional groups on the nanoparticle surface: epoxides, ketones, aldehydes, lactones, alcohols and carboxylic acids. Having the total oxygen content of the carbon nanoparticle distributed among different functionalities results in lower carboxylic acid content and can result in undesired side products during further functionalization of the nanoparticles.

Methods to generate carboxylic acids selectively from the wide variety of oxygen-containing functional groups present on a carbon nanoparticle surface after oxidation, in particular acid oxidation, and the surface-functionalized carbon nanoparticles made by the methods are disclosed herein. The methods result in carbon nanoparticles that are greatly enriched in the number of surface carboxylic acid groups compared to the number obtained by the non-specific oxidation processes currently used. Additionally, the carboxylic acid-functionalized carbon nanoparticles obtained by the methods are readily further derivatized with other functional groups, such as by carbodiimide conjugation, with increased efficiency and yield.

In an aspect, a method of increasing the density of carboxylic acids on a surface of a carbon nanoparticle is disclosed. The method comprises contacting an oxygen-containing functional group on a surface of a carbon nanoparticle with a reducing agent to provide a hydroxyl group; reacting the hydroxyl group with a diazoacetate ester in the presence of a transition metal catalyst to provide an ester, the diazoacetate ester having the structure

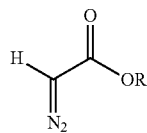

wherein R is a $C_{1-8}$ hydrocarbyl, preferably t-butyl, methyl, ethyl, isopropyl, allyl, benzyl, pentafluorophenyl, or N-succinimidyl; and cleaving the ester to provide a carboxylic acid group.

The carbon nanoparticle can be any carbonaceous material having an average smallest dimension (e.g., a diameter) of 100 nanometers (nm) or less. As used herein, "carbonaceous" means a structure defined primarily by carbon-carbon bonds, although other elements can be present, for example trace amounts (e.g., a catalyst residue) or as functional groups (e.g., oxygen-containing functional groups as described below. The carbon nanoparticle can be a carbon nanotube, a fullerene, graphene, graphene oxide, a nanodiamond, or a combination thereof. In some embodiments, the carbon nanoparticle is a nanodiamond, preferably a fluorescent nanodiamond.

A "fullerene", as used herein, can include any of the known cage-like hollow allotropic forms of carbon possessing a polyhedral structure. A fullerene can include, for example, from about 20 to about 100 carbon atoms. For example, $C_{60}$ is a relatively common, commercially available fullerene having 60 carbon atoms.

Carbon nanotubes are tubular fullerene structures having open or closed ends and which are made entirely or partially of carbon, and can include also components such as metals, metalloids or ceramics. Carbon nanotubes can be single walled nanotubes (SWNTs) or multi-walled nanotubes (MWNTs).

Graphene can be a single sheet or several sheets of graphite having nano-scale dimensions, in particular thickness. Graphene has a plate-like two dimensional structure of fused hexagonal rings with an extended delocalized π-electron system, layered and weakly bonded to one another through pi-pi stacking interaction. Nanographene can be prepared by exfoliation of nanographite or by catalytic bond-breaking of a series of carbon-carbon bonds in a carbon nanotube to form a nanographene ribbon by an "unzipping" process, followed by derivatization of the nanographene to prepare, for example, nanographene oxide.

"Diamond" as used herein includes both natural and synthetic diamond from a variety of synthetic processes, as well as "diamond-like carbon" (DLC) in particulate form. The term "fluorescent nanodiamond" (FND) refers to nanodiamonds that exhibit fluorescence when exposed to an appropriate absorption (excitation) spectrum. Fluorescent nanodiamonds are commercially available from a number of sources, e.g. Adámas Nanotechnologies (Raleigh, N.C.) or Sigma-Aldrich. The carbon nanoparticles used in the method have, or are treated to have, at least one oxygen-containing group having a carbon-oxygen bond, and that is not a carboxylic acid. In a particularly advantageous feature, the carbon nanoparticles can have more than one type, more than two types, or any number of types of such oxygen-containing groups. Examples of these oxygen-containing groups include alkyl hydroxyl groups, most commonly methylol groups, aldehyde groups, and epoxide groups. Methods for introducing oxygen-containing groups that contain a carbon-oxygen bond are known in the art, and include, for example, treatment of the carbon nanoparticles with a strong mineral acid such as sulfuric acid, nitric acid, or a combination thereof.

In the method, the various oxygen-containing groups on the nanoparticle surface are first reduced to alcohols using a reducing agent effective to convert the oxygen-containing group. Where more than one type of oxygen-containing group is present, the reducing agent is a strong, non-selective reducing agent that is effective to convert all, or nearly all, of the oxygen-containing groups to a group containing a C—OH bond. The reducing agent can be a metal hydride. Examples of metal hydrides include lithium triethylborohydride ($LiBHEt_3$), $LiAlH_4$, $AlH_3$, $Al(BH_4)_3$ ($NaBH_4+AlCl_3$), $LiBH_4$, $Mg(BH_4)_2$ ($NaBH_4+MgCl_2$), $Ca(BH_4)_2$ ($NaBH_4+CaCl_2$), $Na/NH_3$, $Li/NH_3$, $Ca/NH_3$, or a combination thereof. The strong non-selective reducing agent converts most of the oxygen-containing functional groups into alcohols (see, Nystrom, R. F.; Brown, W. G., Reduction of Organic Compounds by Lithium Aluminum Hydride. I. Aldehydes, Ketones, Esters, Acid Chlorides and Acid Anhydrides. *Journal of the American Chemical Society* 1947, 69 (5), 1197-1199; Nystrom, R. F.; Brown, W. G., Reduction of Organic Compounds by Lithium Aluminum Hydride. II. Carboxylic Acids. *Journal of the American Chemical Society* 1947, 69 (10), 2548-2549.).

The reduction can be carried out in an aprotic nonpolar solvent with sonication to maximize the exposed surface area. Examples of a suitable solvent include tetrahydrofuran (THF), 2-methyltetrahydrofuran (2-MeTHF), acetonitrile, 1,2-dimethoxyethane, glyme, diglyme, and dioxane. The reduction reaction is performed at a temperature and for a time selected to provide surface alcohols in high yield. For example, the temperature of the reduction reaction can be 55° C. to 80° C., 60° C. to 75° C., 65° C. to 70° C. The reduction reaction can be performed for 24 to 72 hours, 36 to 60 hours, 44 to 52 hours, or for any other time required to obtain a high yield of hydroxyl groups, i.e., groups containing a C—OH bond.

The reduction reaction can be quenched by reducing the temperature, for example to room temperature or lower, by the addition of 1 M HCl, or other suitable acid, or other methods known in the art. The reduced nanoparticles can be washed one or more times to remove any metal salts that form from the reduction reaction. Washing the reduced particles can be performed with an acid at 1 N, a base at 1 N, and/or distilled water. In some embodiments, the acid is HCl and the base is NaOH.

The reduced nanoparticles are contacted with a diazoacetate ester in the presence of a transition metal catalyst and solvent to provide a surface-functionalized ester attached to the nanoparticle surface via an ether linkage formed with the surface alcohol group (see, Aller, E.; Brown, D. S.; Cox, G. G.; Miller, D. J.; Moody, C. J., Diastereoselectivity in the O—H Insertion Reactions of Rhodium Carbenoids Derived from Phenyldiazoacetates of Chiral Alcohols. Preparation Of .Alpha.-Hydroxy And .Alpha.-Alkoxy Esters. The *Journal of Organic Chemistry* 1995, 60 (14), 4449-4460.). Examples of the transition metal catalyst include $Rh_2(OAc)_4$, $Rh_2(NHAc)_4$, $Rh_2(NHCOCF_3)_4$, $Rh_2(NHCOC_3F_7)_4$, $Cu(OTf)_2$, $CuI.P(OMe)_3$, $Ni(acac)_2$, $BF_3.Et_2O$, or a combination thereof, wherein Ac is acetate, Tf is triflate, Me is methyl, acac is acetylacetate, and Et is ethyl. In preferred embodiments, the transition metal catalyst can be $Rh_2(OAc)_4$, $Rh_2(NHAc)_4$, or a combination thereof.

Examples of a suitable solvent for the reaction include benzene, toluene, xylene(s), hexane, cyclohexane, dichloromethane, and ethyl acetate. The diazoacetate ester is selected to permit subsequent hydrolysis to the carboxylic acid to proceed with good efficiency and yield. Examples of the diazoacetate ester include tert-butyl diazoacetate, methyl diazoacetate, ethyl diazoacetate, isopropyl diazoacetate, allyl diazoacetate, benzyl diazoacetate, pentafluorophenyl diazoacetate, and N-succinimidyl diazoacetate. The reaction is performed at a temperature and for a time selected to obtain insertion of the surface alcohols into the diazoacetate ester and formation of the ether linkage in high yield. For example, the temperature of the reaction can be 25° C. to 95° C., 45° C. to 90° C., 65° C. to 85° C., 75° C. to 80° C. The reaction can be performed until the reaction is complete, for example for 24 to 72 hours, or 36 to 60 hours, or 44 to 52 hours.

The ester-derivatized nanoparticles can be washed one or more times with a solvent to remove any excess diazoacetate ester and the transition metal catalyst. Examples of suitable solvents include dichloromethane, methanol, and a combination thereof. Optionally the washed nanoparticles are dried.

The ester-derivatized nanoparticles can be subjected to cleavage of the ester, e.g., by hydrolysis, to generate a carboxylic acid. Methods for ester cleavage are known. In preferred embodiments, acid hydrolysis of the ester is used to generate a carboxylic acid. For example, a neat trifluoroacetic acid treatment can be used to cleave the ester on the ester-derivatized nanoparticles and generate a carboxylic acid. Other methods of hydrolysis may include other acids such as hydrochloric acid (1N, 3N, or 6N). Alternatively the esters can be cleaved by base hydrolysis using sodium or potassium hydroxide. The carboxylic acid-functionalized carbon nanoparticles can be washed one or more times and optionally dried. Washing can be with a solvent such as methanol, dichloromethane, water, or a combination thereof.

The disclosed method for enhancement of carboxylic acids on the surface of the carbon nanoparticles, e.g., nanodiamonds, is modular, and thus permits the generation of a wide array of biologically active surface groups attached to the nanoparticle surface. Optionally, a polyethylene glycol (PEG) or an alternative linker can be used to couple a molecule of interest to a carboxylic acid on the surface of the nanoparticle. The PEG linker can have an average molecular weight of up to 8000, up to 6000, up to 5000. The PEG linker length can be 2 to 180 ethylene glycol units, 2 to 100 ethylene glycol units, 2 to 50 ethylene glycol units, 2 to 43 ethylene glycol units, or 3 to 36 ethylene glycol units, or 3 to 12 ethylene glycol units. Any other suitable linker known in the art can be used.

Thus the method can further comprise functionalizing the carboxylic acid group to a second functional group. Any suitable methods known in the art for further functionalizing the carboxylic acid-functionalized nanoparticles can be used. Examples of second functional groups include an acyl chloride, an amide, a pegylate, a biotinylate, a folate, a thiol, a protected thiol, a maleimide, an active ester, an amine, a chelated gadolinium, a functional group for click chemistry, an alkylating group, a protein tag system ligand, and a dendrimer linkage. Examples of a click chemistry functional group include an azide and an alkyne. Alkylating groups include maleimides, bromo or chloracetyl groups, α,β-unsaturated esters and amides, substituted epoxides, acid chlorides, and other alkylating groups typically used in the field. Examples of commercially available protein tag systems include HALOTAG (a modified haloalkane dehalogenase, Promega Corporation) and SNAP-TAG (a 20 kDa mutant of $O^6$-alkylguanine-DNA alkyltransferase) and its derivative CLIP-TAG (both from New England Biolabs, Inc.). (See, Hoehnel, S; Lutolf, M. P., Capturing Cell-Cell Interactions via SNAP-tag and CLIP-tag Technology. *Bioconjugate Chemistry* 2015, 26, 1678-1686; Moon, W. K.; Lin, Y.; O'Loughlin, T.; Tang, Y.; Kim, D.-E.; Weissleder, R.; and Tung, C.-H., Enhanced Tumor Detection Using a Folate Receptor-Targeted Near-Infrared Fluorochrome Conjugate. *Bioconjugate Chemistry* 2003, 14, 539-545.) Examples of ligands for these protein tag systems include compounds comprising a haloalkane moiety for the HALOTAG system; compounds comprising an $O^6$-alkylguanine moiety for the SNAP-TAG system, and compounds comprising an $O^2$-benzylcytosine moiety for the CLIP-TAG system.

For example the surface carboxylic acid groups of the nanoparticles can be further functionalized to acyl chlorides. For example, the nanoparticles can be contacted with thionyl chloride under conditions resulting in conversion of the carboxylic acid to an acyl chloride. For example, the nanoparticles can be suspended in neat thionyl chloride and held at a temperature of 65-75 C to convert the carboxylic acid to an acyl chloride. Alternatively, $POCl_3$ can be used.

The acyl chloride-functionalized nanoparticle is reactive to amines, permitting formation of amides. For example an acyl chloride-functionalized nanoparticle can be contacted with an amine, $NH_2R$ in the presence of a catalytic amount of 4-dimethylaminopyridine (DMAP) in DCM to produce the amide.

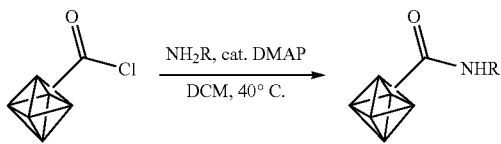

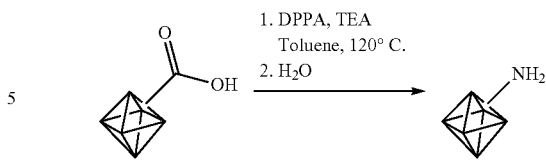

Such reactions can be used to covalently attach a large number of moieties of potential interest to the nanoparticle. For example, the amine can be an O-(2-Aminoethyl)-O'-(2-azidoethyl)pentaethylene glycol (amine-PEG-azide) or a biotinylated polyethylene glycol amine, having structure:

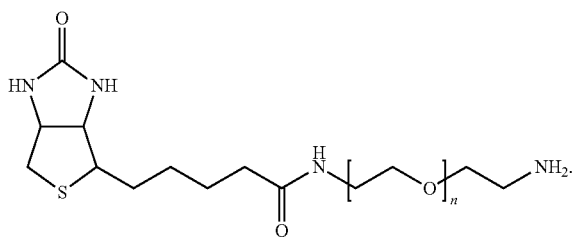

The surface carboxylic acid groups of the nanoparticles can also be functionalized to amides via alternative reaction routes. For example the surface carboxylic acid groups can be reacted with reagents such as N-(3-dimethylaminopropyl)-N-ethyl-carbodiimide hydrochloride (See Fu, C. C., Lee, H. Y., Chen, K. C., Lim, T. S., Wu, H. Y., Lin, P. K., Wei, P. K., Tsao, P. H., Chang, H. C., Fann, W. Characterization and application of single fluorescent nanodiamonds as cellular biomarkers. *Proceedings of the National Academy of Sciences of the United States of America,* 2007, 104(3), 727-732.). Carbodiimide compounds provide the most popular and versatile method for labeling or crosslinking to carboxylic acids. The most readily available and commonly used carbodiimides are the water-soluble 1-ethyl-3-(3-dimethylaminopropyl)carbodiimide (EDC) for aqueous crosslinking and the water-insoluble dicyclohexyl carbodiimide (DCC) for non-aqueous organic synthesis methods. These carbodiimides work by activating carboxyl groups for direct reaction with primary amines via amide bond formation. No portion of their chemical structure becomes part of the final bond between conjugated molecules. EDC is often used in combination with N-hydroxysuccinimide (NHS) for the immobilization of large biomolecules. NHS, or its water-soluble analog (sulfo-NHS), when included in EDC coupling protocols, improves efficiency or creates dry-stable (amine-reactive) intermediates.

The surface carboxylate groups can also be pegylated and further derivatized (See Chang, B. M., Lin, H. H., Su, L. J., Lin, W. D., Lin, R. J., Tzeng, Y. K, Lee, R. T., Lee, Y. C., Yu, A. L., Chang, H. C., Highly Fluorescent Nanodiamonds Protein-Functionalized for Cell Labeling and Targeting. *Advanced Functional Materials* 23(46): 5737-5745.).

The surface carboxylic acid groups can also be converted to amine groups. For example, the surface carboxylic acid groups can be converted to surface amines by reaction with diphenylphosphoryl azide (DPPA) and triethylamine (TEA) in the presence of a nonpolar solvent such as toluene.

In another aspect, a surface-functionalized carbon nanoparticle is disclosed.

The surface-functionalized carbon nanoparticle comprises a first functional group attached to a surface of the carbon nanoparticle, wherein the first functional group is present in an amount of at least $0.8 \times 10^{17}$ first functional group/g of carbon nanoparticle, at least $1 \times 10^{17}$, at least $3 \times 10^{17}$, at least $5 \times 10^{17}$, at least $7 \times 10^{17}$, or at least $9 \times 10^{17}$, preferably $3-5 \times 10^{17}$ first functional group/g of carbon nanoparticle measured for diamond nanoparticles of 80 nm in diameter. The surface-functionalized carbon nanoparticle comprises a first functional group attached to a surface of the carbon nanoparticle, wherein the first functional group is present in an amount of at least 80 first functional group/carbon nanoparticle, at least 100, at least 300, at least 500, at least 700, or at least 900, preferably 300 to 500 first functional group/carbon nanoparticle, measured for diamond nanoparticles of 80 nm in diameter. A surface density of 300 to 500 first functional group/carbon nanoparticle can also be expressed as one functional group per 40-70 nm$^2$, which is referred to as the "parking area". Examples of the first functional group include a carboxylic acid, an acyl chloride, an amide, a pegylate, a biotinylate, or an amine. The first functional group can be further functionalized to a second functional group. Examples of the second functional group include an acyl chloride, an amide, a pegylate, a biotinylate, a folate, a thiol, a maleimide, an active ester, an amine, a chelated gadolinium, an azide, an alkyne, a protein tag ligand, or a dendrimer linkage.

As is known in the art, accurate determination of particle dimensions in the nanometer range can be difficult. In an embodiment, the dimension of the nanoparticles is determined using their hydrodynamic diameter. The hydrodynamic diameter of the nanoparticle or an aggregate of nanoparticles can be measured in a suitable solvent system, such as an aqueous solution. The hydrodynamic diameter can be measured by sedimentation, dynamic light scattering, or other methods known in the art. In an embodiment, hydrodynamic diameter is determined by differential centrifugal sedimentation. Differential centrifugal sedimentation can be performed, for example, in a disc centrifuge. In an embodiment, the hydrodynamic diameter is a Z-average diameter determined by dynamic light scattering. The Z-average diameter is the mean intensity diameter derived from a cumulants analysis of the measured correlation curve, in which a single particle size is assumed and a single exponential fit is applied to the autocorrelation function. The Z-average diameter can be determined by dynamic light scattering with the sample dispersed in, for example, deionized water. An example of a suitable instrument for determining particle size and/or the polydispersity index by dynamic light scattering is a Malvern Zetasizer Nano.

The following examples are merely illustrative of the methods disclosed herein, and are not intended to limit the scope hereof.

EXAMPLES

Example 1. Enrichment of Surface Density of Carboxylic Acids on Carbon Nanoparticles Experiments were performed to increase the surface density of carboxylic acid groups on a representative oxidized carbon nanoparticle, a nanodiamond, illustrated schematically in Scheme 1.

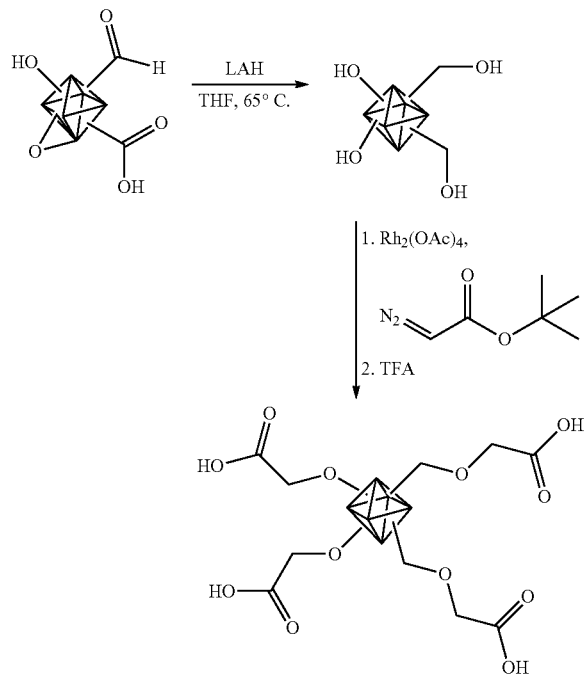

In Scheme 1, an acid oxidized nanodiamond (diamond) containing a variety of oxygen-containing groups is treated with a non-selective reducing agent, such as $LiAlH_4$ (LAH) to reduce the oxygen-containing surface functional groups to primarily alcohols. This is followed by a rhodium (II) acetate ($Rh_2(OAc)_4$) catalyzed carbenoid insertion reaction to provide a t-butyl oxyacetyl group, where the t-butyl acetyl group is attached to the nanodiamond via an ether bond. The final step is cleavage of the t-butyl group from the ester to generate carboxylic acids on the nanodiamond surface. A more detailed description of the reaction scheme is provided below.

A quantity (70 mg) of detonation nanodiamonds (Adámas Nanotechnologies; ND-COOH: 60-80 nm) was placed in a glass vial along with a Teflon-coated stir bar and dried under vacuum by heating with a heat gun for ten minutes. The dried diamonds were allowed to cool under an argon environment. Upon cooling, 3 mL of a 1 M lithium aluminum hydride solution in tetrahydrofuran (THF) (Sigma-Aldrich) was added into the vial slowly. The vial was sealed and sonicated to disperse the diamonds in the THF solution. The reduction reaction was kept at 65° C. for 48 hours with vigorous stirring. After the reaction was complete, the dispersion was cooled in an ice bath and quenched slowly with drop-wise addition of 1 M HCl. The diamonds were then thoroughly washed with 1 M HCl, 1 M NaOH, and finally deionized (DI) water until the pH of the supernatant was slightly less than seven. The reduced diamonds were then lyophilized into a powder form in order to obtain an IR spectrum.

Subsequently, 50 mg of the reduced diamonds and a Teflon-coated stir-bar were placed into a glass vial and again dried under vacuum using a heat gun for ten minutes. After heating, the dried diamonds were allowed to cool in an argon environment. The diamonds were then dispersed in 1.5 mL anhydrous benzene (Sigma-Aldrich) through sonication and stirring. To this suspension, 1.5 mg of rhodium (II) acetate dimer (Sigma-Aldrich) and 20 µL of tert-butyl diazoacetate (Sigma Aldrich) were added. The vial was flushed with argon, sealed, and kept at 80° C. for 48 hours. The diamonds were subsequently isolated by centrifugation and washed thoroughly with dichloromethane (Sigma-Aldrich) to remove any unreacted reagents. The diamonds were then allowed to dry for several hours under vacuum. After drying, 48 mg of the diamonds were transferred into a glass vial along with a Teflon-coated stir bar and 2 mL of 99% trifluoroacetic acid (TFA) (Sigma-Aldrich) was added. The diamonds were dispersed in the trifluoroacetic acid by sonication. After two days at room temperature in the trifluoroacetic acid, the diamonds were again isolated by centrifugation and washed thoroughly with water and methanol and dried under vacuum. A small amount of the diamonds was used to obtain an FTIR spectrum.

Figure 2:
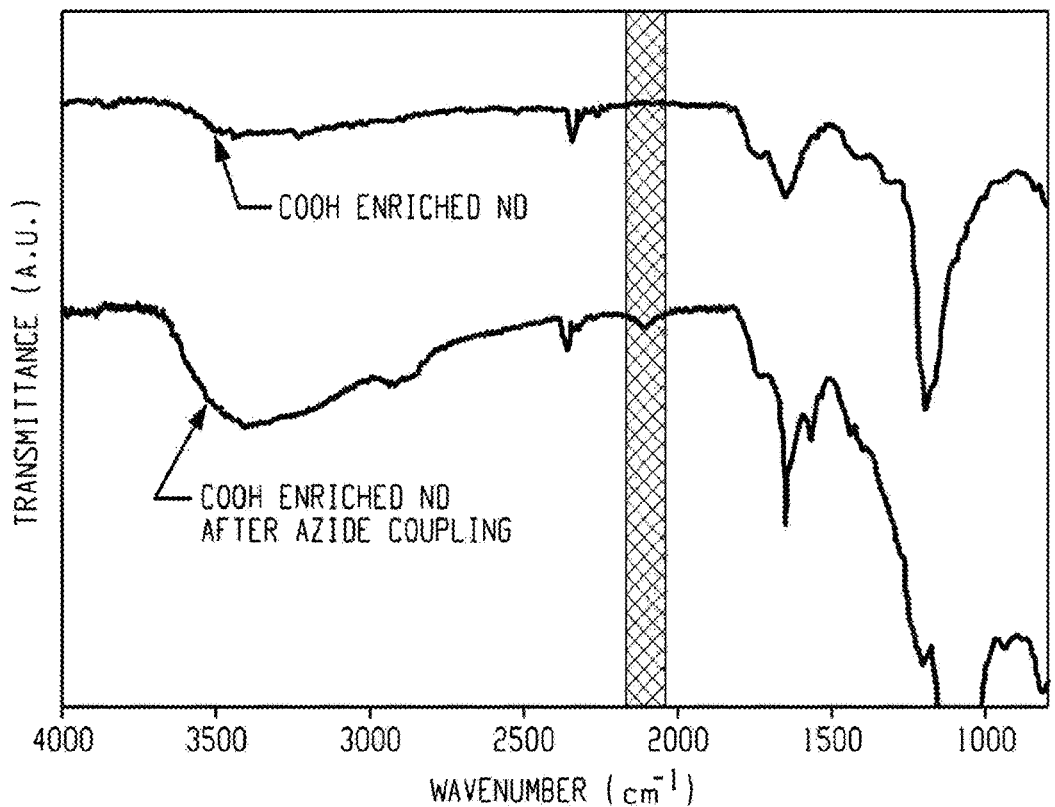
FIG. 2 presents Fourier transform infrared (FTIR) spectra of nanodiamonds that have been carboxylic acid enriched by the reduction and carbenoid insertion reactions (upper spectrum) and subsequently coupled with amine-PEG-azide (bottom spectrum). The vertical grey area highlights the expected azide stretching peak at ~2100 $cm^{-1}$.

The reduction of oxygen-containing groups into alcohols and the subsequent formation of carboxylic acids on detonation nanodiamond surfaces were tracked by Fourier-transform infrared spectroscopy (FTIR) (FIG. 2). The spectra in FIG. 1 correspond to untreated detonation nanodiamonds (top spectrum), nanodiamonds reduced with LAH (middle spectrum), and LAH-reduced diamonds following the carbenoid insertion reaction and subsequent ester cleavage (bottom spectrum).

Initially the nanodiamond surface contains many different oxygen-containing functional groups resulting in the presence of both a carbonyl (C=O) stretch at ~1750 cm-1 and a broad O—H stretch centered at ~3400 $cm^{-1}$ (FIG. 1, top spectrum). Upon reduction of the nanodiamonds with LAH, the carbonyl stretch decreases and nearly vanishes while the O—H stretching vibrations at 3400 $cm^{-1}$ along with the O—H bending vibrations at 1650 $cm^{-1}$ dramatically increase (FIG. 2 FIG. 1, middle spectrum). This is consistent with the transformation of carbonyl containing groups such as ketones, aldehydes, lactones, and carboxylic acids into alcohol groups. After the carbenoid insertion reaction and subsequent ester cleavage, the IR spectrum (FIG. 1, bottom spectrum) shows a decrease in the O—H peaks and an increase in the carbonyl peak. This carbonyl peak largely represents carboxylic acids formed from the carbenoid insertion reaction and subsequent ester cleavage whereas the original carbonyl peak was a result of a mixture of oxygen-containing functional groups. This conclusion is supported by the appearance of the strong peak at 1200 $cm^{-1}$ corresponding to the ether bond formed in the carbenoid insertion reaction (FIG. 1 bottom spectrum).

Example 2. Coupling Carboxylic Acid-Enriched Nanodiamonds with Amine-PEG-Azide Experiments were performed to functionalize the carboxylic acid-enriched detonation nanodiamonds made by the method of Example 1 with O-(2-aminoethyl)-0'-(2-azidoethyl)pentaethylene glycol (amine-PEG-azide). Azide has a strong and unique infrared signature around 2150 cm$^{-1}$, allowing for easy verification of subsequent surface functionalization.

The functionalization is shown schematically in Scheme 2.

Scheme 2.

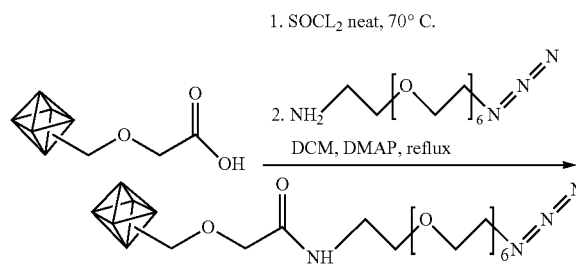

As shown in Scheme 2, thionyl chloride (SOCl$_2$) was used to convert the nanodiamond carboxylic acids into acyl chlorides, followed by reaction of the amine-PEG-azide with the acyl chlorides. Since the nanodiamonds are resistant to harsh environments, thionyl chloride can be used neat, with the diamonds dispersed through sonication. After formation of the acyl chlorides, the diamonds were suspended in dichloromethane and the acyl groups were amidated by addition of amine-PEG-azide, and the catalyst 4-(dimethylamino)pyridine (DMAP) to the suspension.

In particular, carboxylic acid-enriched diamonds (20 mg dried) and a stir bar were dried under vacuum with a heat gun for ten minutes. To this, 7 mL of thionyl chloride (97%, Sigma-Aldrich) was added. The vial was sealed and then sonicated to suspend the diamonds in the thionyl chloride. The dispersion was stirred and heated to 70° C. for 48 hours. The diamond dispersion was allowed to cool to room temperature and then centrifuged (3270×g for 1 hour). The thionyl chloride supernatant was removed and the pellet of acyl chloride-functionalized nanodiamonds was kept under vacuum for four hours to remove residual thionyl chloride. Air exposure was minimized to prevent the reactive acyl chlorides from coming into contact with moisture. The dry acyl chloride-functionalized nanodiamonds (16 mg) were suspended in 1 mL of dichloromethane (DCM) (Sigma-Aldrich). To this, 100 μL of O-(2-aminoethyl)-O'-(2-azidoethyl)pentaethylene glycol (amine-PEG-azide) (Sigma-Aldrich) and 50 mg 4-(dimethylamino)pyridine (DMAP) (Sigma-Aldrich) was added. The diamond dispersion was kept at 39° C. for one day. The diamonds were then isolated by centrifugation and thoroughly washed with DCM and methanol in order to remove unreacted reagents. The diamonds were dried under vacuum and a few milligrams of the dried powder were used to provide an FTIR spectrum.

FIG. 2 shows the FTIR spectrum for a representative sample of the nanodiamonds before (top spectrum) and after (bottom spectrum) amidation of the carboxylic acid groups with the amine-PEG-azide. After amidation of the carboxylic acid groups with the amine-PEG-azide, a prominent azide stretching peak at ~2100 cm$^{-1}$ is clearly visible in the spectrum of the amidated diamonds that was not present in the carboxylic acid-enriched diamonds prior to the amidation reaction. Additionally, the presence of amide 1 and amide 2 peaks at 1650 cm$^{-1}$ and 1570 cm$^{-1}$ indicates covalent attachment of the amine-PEG-azide onto the carboxylic acids. Alkyl peaks at 2870 cm$^{-1}$ and 2930 cm$^{-1}$ are also visible and may arise from the carbon-hydrogen bonds of the PEG linker. The broad peak centered at 3400 cm$^{-1}$ is attributed to hydrogen-bonded N—H vibrations from the amide bond. The presence of these infrared signals indicates that the enriched carboxylic acids can be used as handles for further surface conjugation of nanodiamonds.

Example 3. Biotinylation of Nanodiamonds

To verify that the carboxylic acid content on the surface of nanodiamonds treated with the enrichment process was greater than that of untreated nanodiamonds, the amount of biotinylated polyethylene glycol amine (amine-PEG-biotin) (MW: 5000, Nanocs) (structure below) coupled to unenriched fluorescent nanodiamonds (FNDs) was compared to the amount coupled to FNDs that had undergone the carboxylic acid enrichment procedure.

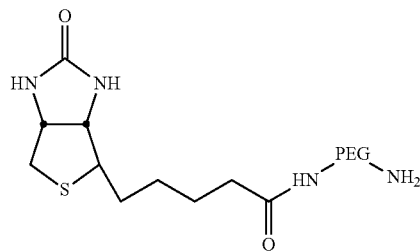

Biotinylation of fluorescent nanodiamonds (FNDs) (Adámas Nanotechnologies, acid treated, Sample 7-1 80 nm diameter FNDs) was performed using amine-PEG-biotin in an identical manner to that described above in Example 2.

Prior to the biotinylation procedure, the FNDs were separated into two batches. One batch was first enriched for surface carboxylic acids following the procedure outlined above in Example 1 (ND-COOH-Enriched) prior to functionalization with the amine-PEG-biotin, while the other batch was used as purchased (ND-COOH) in the functionalization reaction.

Biotin was attached to both batches of diamonds using identical procedures and identical amounts of diamond, dichloromethane, DMAP, and amine-PEG-biotin.

Quantifying Biotin on Nanodiamond Surface.

Figure 3A:
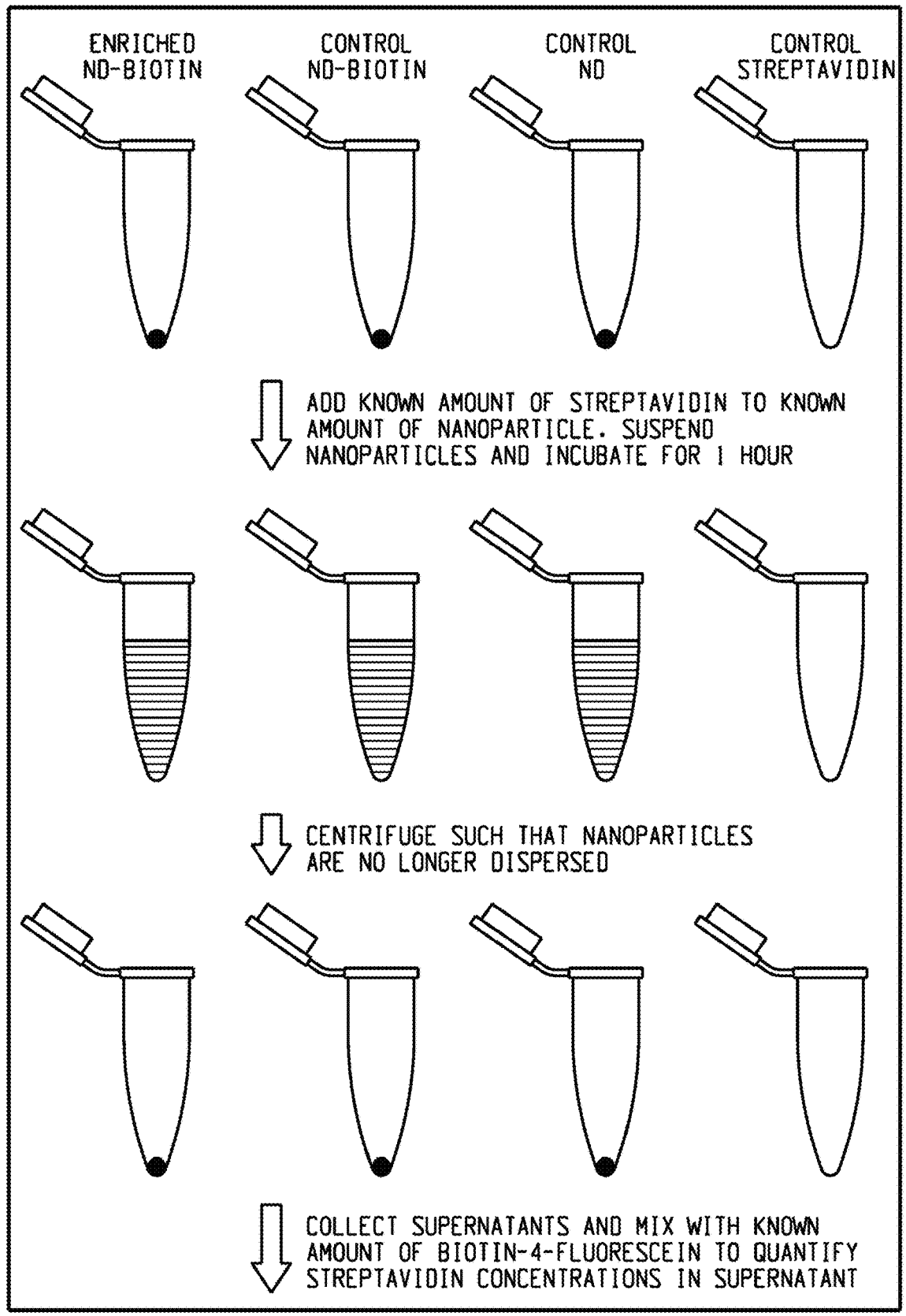
FIG. 3 presents a schematic of the assay used to determine the biotin content on the nanodiamond surfaces (panel A), a graph showing a standard curve of measured fluorescence (plotted as of relative fluorescence units (RFU)) of 20 nM biotin-FITC as a function of streptavidin concentration (panel B), and a dotplot showing the measured fluorescence of a 1:1 mixture of 40 nM biotin-FITC and the supernatant from the Enriched ND-biotin and Control ND-Biotin samples and corresponding streptavidin concentrations of these two solutions is also shown (panel C).
Figure 3B:
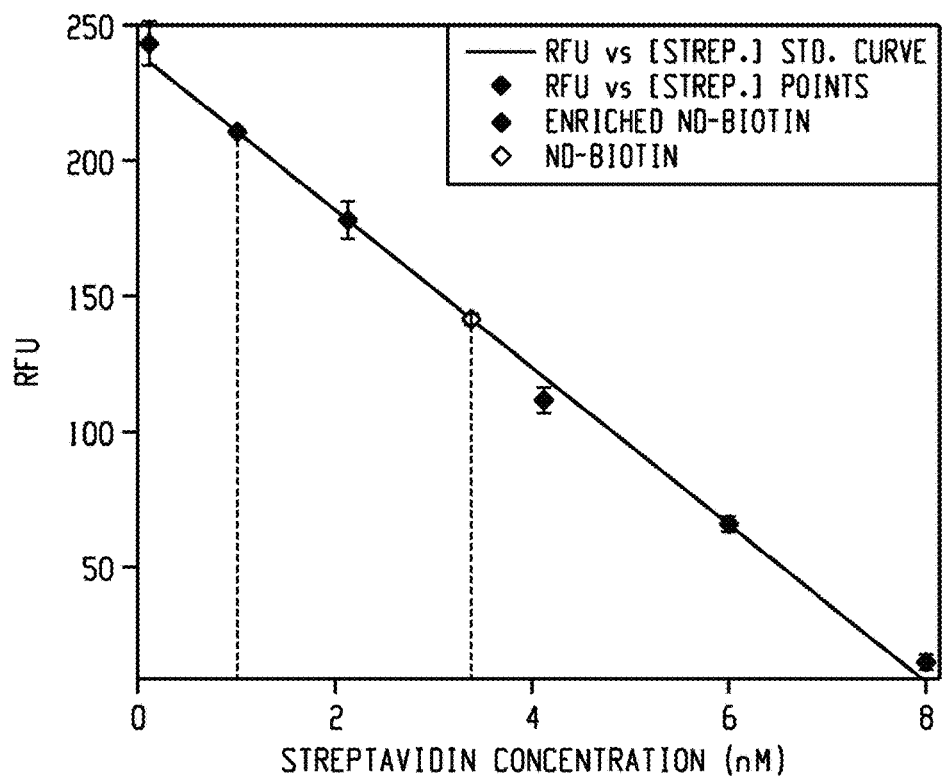
Figure 3C:
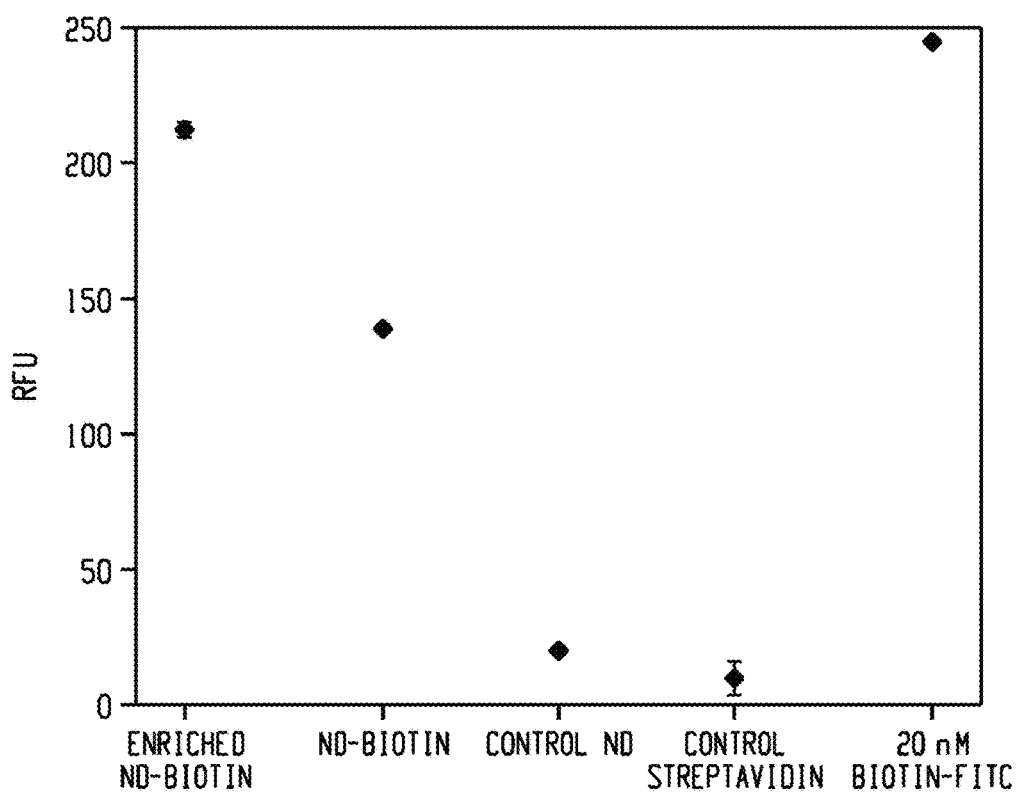

The assay used to determine the amount of biotin present on the nanoparticle surfaces is shown schematically in FIG. 3A. A measured mass of the nanodiamonds was suspended in a known amount of streptavidin solution and the system was allowed to come to equilibrium. The suspensions were then centrifuged, resulting in removal of the diamonds and any bound streptavidin from the supernatant. The supernatants, containing free streptavidin not bound by biotin on the nanoparticles, were collected and quantified. The amount of streptavidin present in the supernatants was quantified using biotin-4-fluorescein (Biotin-FITC). When streptavidin binds biotin-FITC, the fluorescein fluorescence is quenched (FIG. 3B). By comparing the fluorescence intensity of a 1:1 mixture of the supernatant and biotin-FITC with a standardized curve, the biotin content on the nanodiamonds can be calculated.

A known mass of biotinylated enriched nanodiamonds (Enriched ND-Biotin), biotinylated unenriched nanodiamonds (Control ND-biotin) and unfunctionalized nanodiamonds (Control ND) were individually mixed in a 1-to-1 proportion with 160 nM streptavidin (Sigma Aldrich #S4762) in 1× phosphate buffered saline (PBS) with 0.3% bovine serum albumin (BSA) and 0.01% TWEEN-20

(Sigma Aldrich #P9416). The streptavidin solution was added into a separate vial without diamonds as a control for streptavidin binding (Control Streptavidin). The diamonds were dispersed by sonication for ten minutes then slowly shaken for one hour. The diamond dispersions were then centrifuged (13,400×g for 10 minutes) and the supernatants were collected. The streptavidin present in the supernatants was determined by mixing 20 µL of supernatant with 20 µL of a 40 nM solution of biotin-4-fluorescein (biotin-FITC) (Molecular probes, Thermo-Fisher Scientific #B10570), incubating for 15 minutes to allow the free streptavidin to bind the biotin-FITC, and then measuring the fluorescence in a microplate reader (Tecan Spark-10) with excitation at 485 nm and emission at 518 nm. The concentration of streptavidin present in the supernatant was determined by comparing the measured fluorescence with a standard curve of fluorescence intensity of 20 nM biotin FITC as a function of streptavidin concentration. The amount of biotin present on the nanodiamonds was subsequently approximated from the concentration of free streptavidin in the supernatants.

As can be seen in FIG. 3B, the fluorescence of a 1:1 mixture of the supernatant from the enriched ND-Biotin sample and 40 nM biotin-FITC resulted in a fluorescence of 212 RFU, corresponding on the standard curve to a streptavidin concentration of ~0.9 nM in the 1:1 mixture of biotin-FITC and supernatant. Thus, the streptavidin concentration in the supernatant of the enriched ND-Biotin sample was 1.8 nM. Similarly, the streptavidin concentration in the supernatant of the control ND-Biotin sample was calculated to be 6.4 nM. The lower concentration of unbound streptavidin in the supernatant of the enriched ND-Biotin sample compared to the supernatant of the control ND-Biotin sample is consistent with an increase in surface-functionalization with biotin on the enriched nanodiamonds compared to the control nanodiamonds.

Example 4. Enrichment of Surface Density of Carboxylic Acids on Carbon Nanotubes The surface of acid-treated carbon nanotubes with a variety of surface oxygen-containing functional groups are enriched for carboxylic acids using a procedure in general accordance with Example 1.

The oxygen-containing functional groups on the surface of the carbon nanotubes are first reduced to hydroxyl groups with lithium aluminum hydride solution in THF. The reduced nanotubes are then treated with the rhodium (II) acetate dimer and tert-butyl diazoacetate to provide t-butyl acetate ester modified nanotubes. The nanotubes are dried and dispersed in trifluoroacetic acid to hydrolyze the t-butyl group and provide carboxylate modified nanotubes.

Example 5. Commercial FNDs are Resistant to Carboxylic Acid Functionalization Commercially purchased detonation nanodiamonds (Adamas Nanotech) have been successfully and routinely functionalized via carbodiimide chemistry; however, fluorescent nanodiamonds (Adámas Nanotechnologies 7-1, 80 nm diameter) could not be functionalized with carbodiimide chemistry.

As shown in Table 1 below, attempts to functionalize commercial FNDs via carbodiimide reactions, in aqueous or nonaqueous solvents, were unsuccessful. Coupling reactions with the alternative reagents 2-(1H-benzotriazol-1-yl)-1,1,3,3-tetramethyluronium hexafluorophosphate (HBTU) or 1-cyano-2-ethoxy-2-oxoethylidenaminooxy)dimethyl-amino-morpholino-carbenium hexafluorophosphate (COMU) were also unsuccessful. Without being bound by theory, this inability to functionalize the surface may be attributable to differences in the surface density of carboxylic acid groups on the fluorescent nanodiamonds compared to detonation diamonds.

TABLE 1

Coupling reactions attempted with commercial FNDs

| Coupling Agent | Solvent | pH | amine- | Successful (?) |
|---|---|---|---|---|
| EDC/NHS | Water | 11 | PEG107-biotin | No |
| EDC/NHS | Water | 10 | PEG107-biotin | No |
| EDC/NHS | Water | 7.6 | PEG107-biotin | No |
| EDC/NHS | Water | 11 | PEG6-azide | No |
| EDC/NHS | Water | 7.6 | PEG6-azide | No |
| EDC/NHS | DMF | — | PEG107-biotin | No |
| EDC/NHS | DMF | — | PEG6-azide | No |
| HBTU | DMSO | — | PEG6-azide | No |
| COMU | DMF | — | PEG6-azide | No |

In contrast, carbodiimide coupling schemes worked efficiently on commercial FNDs subjected to the method described above having increased surface density of carboxylic acid groups, without alteration of their fluorescent properties.

Example 6. Quantitative Comparison of Biotin Functionalization of Fluorescent Nanodiamonds with and without the Carboxylic Acid Enhancement Reaction The biotin-FITC assay described in Example 3 suffers from background issues and proved to be difficult to extend to quantitative assessment of the biotin loading on the nanodiamonds. A more quantitative and robust assay that relies on the aggregation of biotinylated nanoparticles with the addition of sub-saturating amounts of streptavidin has been developed. Because the streptavidin is tetravalent, under conditions where all of the surface bound biotins are not saturated with streptavidin, the nanodiamonds will aggregate. If the diamonds are mixed with increasing concentrations of streptavidin and the size of the particles measured (via dynamic light scattering) after a suitable incubation period, then a characteristic curve is seen in which the size increases with increasing streptavidin concentration up to a critical concentration at which the measured size decreases to a value close to, but slightly larger than the original size. This critical concentration is, to a good approximation, the concentration of accessible biotin on the sample.

Figure 4:
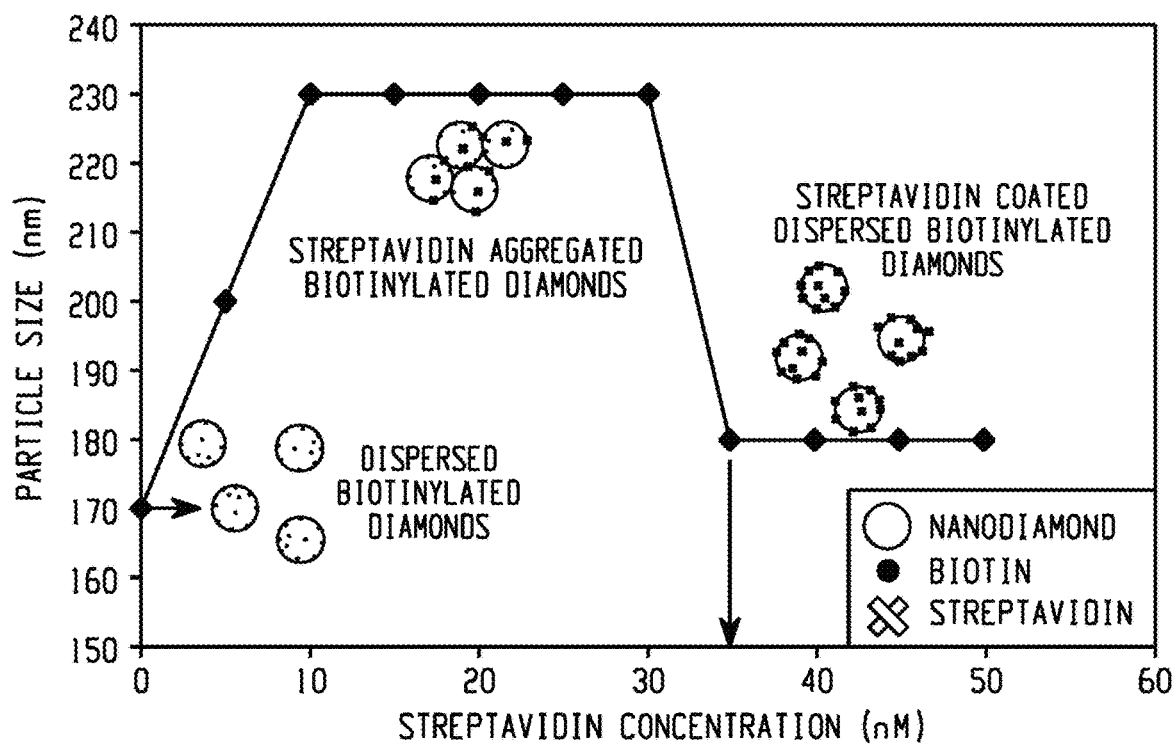
FIG. 4 is a schematic illustration of the aggregation assay to measure surface bound biotin on nanodiamonds.

FIG. 4 is a schematic illustration of the assay to measure biotinylation of nanodiamonds by streptavidin concentration-dependent aggregation and disaggregation. Cuvette-based dynamic light scattering (DLS) with a Wyatt DynaPro NanoStar is used to determine the hydrodynamic radius of a 50 µl sample of 0.05 mg/ml diamonds suspended in phosphate buffered saline (PBS) buffer. Average particle size (intensity-weighted average hydrodynamic radius) is measured by regularization methods as a function of increasing concentration of streptavidin. Without streptavidin (0 nM in FIG. 4), the diamonds are dispersed and have a particular average particle size. For concentrations of streptavidin below the surface bound concentration of biotin, the diamonds aggregate via streptavidin crosslinking and the average particle size increases. Once the streptavidin concentration is equal to the biotin concentration, the diamonds begin to disperse again and the average particle size decreases. The concentration of biotin is well approximated by the concentration of streptavidin at which the size decreases, indicated for the carboxylic acid enriched FNDs by the vertical arrow in FIG. 4.

Figure 5:
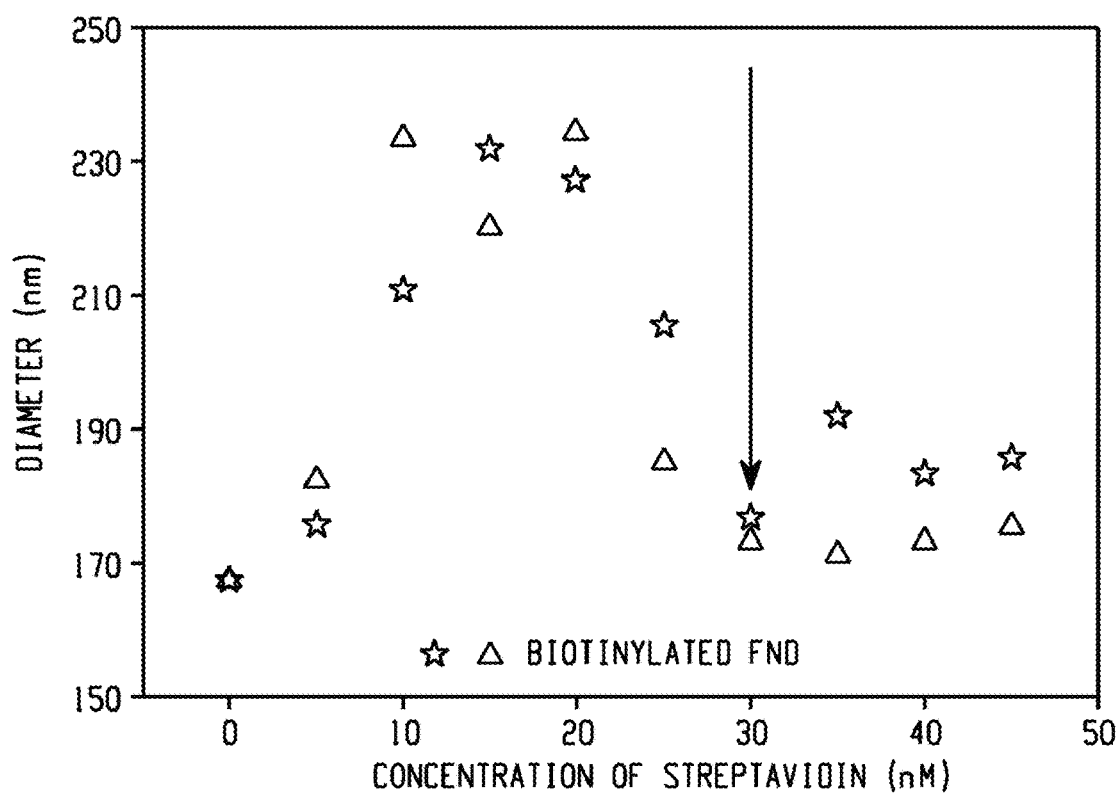
FIG. 5 is a graph of average particle size (diameter (nm)) of biotin-functionalized FNDs as a function of added streptavidin concentration (nM). Two independent measurements of identical biotinylated diamonds (triangles and stars) are shown.

Control experiments with biotin-labeled FNDs were performed and show that the technique is reproducible. The results of these experiments are shown in FIG. 5. FIG. 5 demonstrates the reproducibility of the measured value of the biotin label on the FNDs. Two independent measurements of the same batch of biotin-functionalized FNDs return a critical streptavidin concentration of 30 nM. Combining this surface bound concentration of biotin with the concentration of the nanodiamonds provides a measure of the number of biotins per FND. The FND concentration can be estimated from the combination of FND radius, diamond density, and the mass density used in the DLS measurements, which gives a concentration in the DLS measurements of 90 pM, or from direct measurements of the FND concentration with a Nanosight 300 (Malvern) instrument that counts particles in a defined volume of solution, which gives a concentration of 60 pM in the DLS measurements. Together these data indicate a surface density of 300-500 biotins per diamond particle. Alternatively, the surface density can be expressed as $3-5 \times 10^{17}$ functional group/g of 80 nm diameter carbon nanoparticles, corresponding to 1 functional group per 40-70 $nm^2$ on the surface of the nanodiamond.

This biotinylation assay was used to compare the biotin labeling density of carboxylic acid enhanced nanodiamonds, made by the disclosed method, with the biotin labeling density of nanodiamonds that were not subjected to the surface carboxylic acid enhancement method. The enhanced diamonds and the unenhanced diamonds were each labeled using an identical biotin labeling reaction.

Figure 6A:
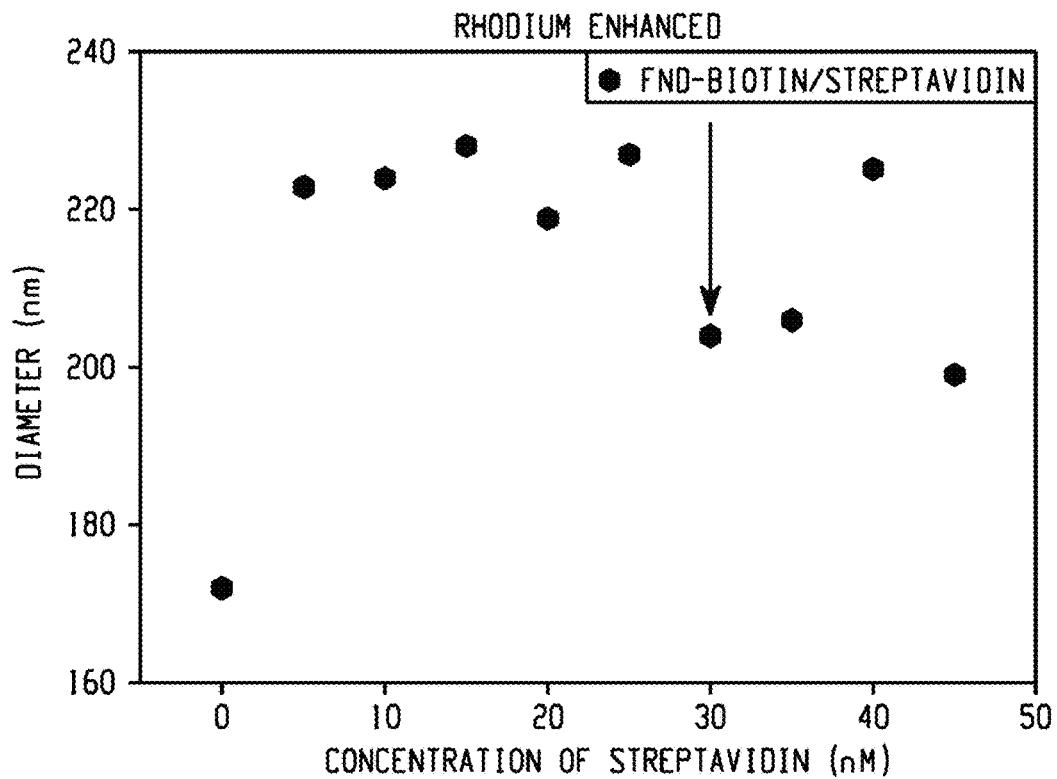
FIG. 6 presents two graphs comparing the streptavidin titration results following carboxylic acid based PEG-biotin labeling for a sample of carboxylic acid-enhanced fluorescent nanodiamonds (left panel) and a sample of unenhanced fluorescent nanodiamonds (right panel).
Figure 6B:
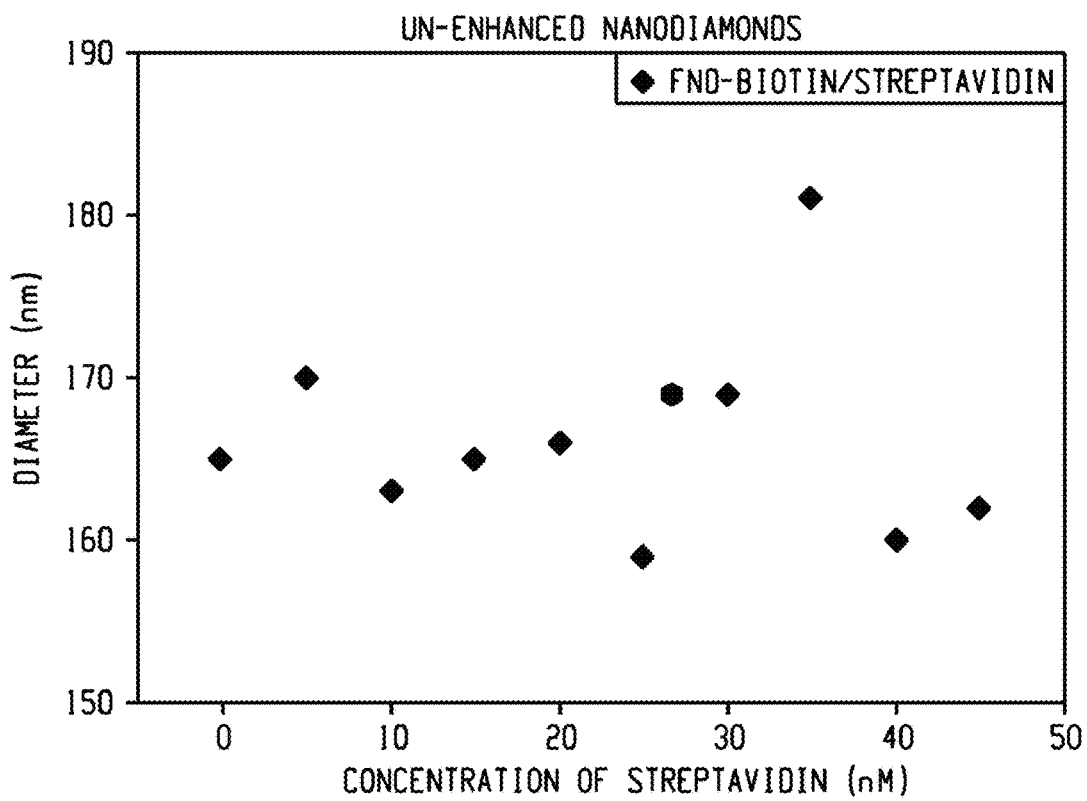

The assay results are shown in FIG. 6. The enhanced diamond sample (left panel) exhibits a biotin concentration of ~30 nM (arrow), whereas the sample that was not subjected to the enhancement process (right panel) does not exhibit a measurable biotin concentration as there was essentially no change in the average particle diameter with increasing streptavidin concentration.

Example 7. Coupling Acid Chloride-Enriched Nanodiamonds with Amine-PEG-Alkyne

Experiments are performed to functionalize the carboxylic acid-enriched detonation nanodiamonds made by the method of Example 2 with commercially available alkyne-PEG4-amine. The alkyne has a strong and unique infrared signature around 3324 $cm^{-1}$, and 2126 $cm^{-1}$, allowing for easy verification of subsequent surface functionalization.

The functionalization is shown schematically in Scheme 3.

Scheme 3.

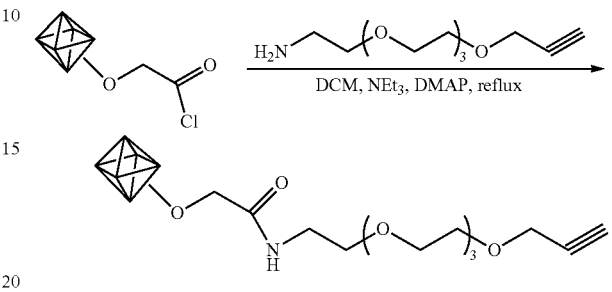

As shown in Scheme 3, the nanodiamond acyl chloride of example 2 is suspended in dichloromethane and the acyl groups are amidated by addition of amine-PEG4-alkyne, triethyl amine, and the catalyst 4-(dimethylamino)pyridine (DMAP) to the suspension.

In particular, the dry acyl chloride-functionalized nanodiamonds (16 mg) are suspended in 1 mL of dichloromethane (DCM) (Sigma-Aldrich). To this, amine-PEG4-alkyne (2 mg) (Click Chemistry Tools), triethylamine (100 µl), and 4-(dimethylamino)pyridine (DMAP, 5 mg) (Sigma-Aldrich) are added. The diamond dispersion is kept at 39° C. for one day. The diamonds are then isolated by centrifugation and thoroughly washed with DCM and methanol in order to remove unreacted reagents. The diamonds are dried under vacuum.

Example 8. Coupling Acid Chloride-Enriched Nanodiamonds with Amine-PEG-dibenzocyclooctynes (DBCO)

Experiments are performed to functionalize the carboxylic acid-enriched detonation nanodiamonds made by the method of Example 2 with commercially available DBCO-PEG4-amine. The alkyne has a strong and unique infrared, allowing for easy verification of subsequent surface functionalization.

The functionalization is shown schematically in Scheme 4.

Scheme 4.

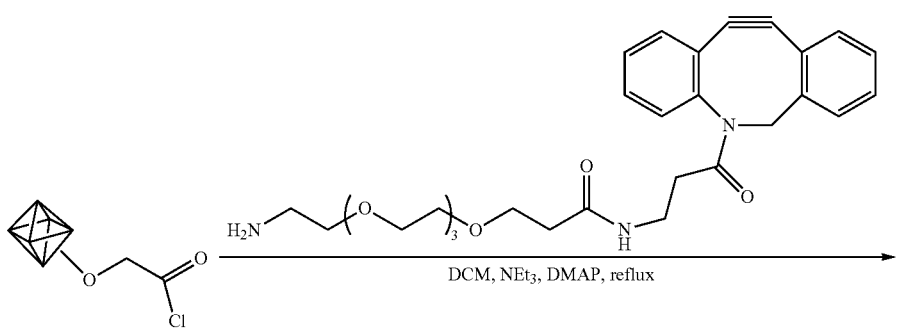

-continued

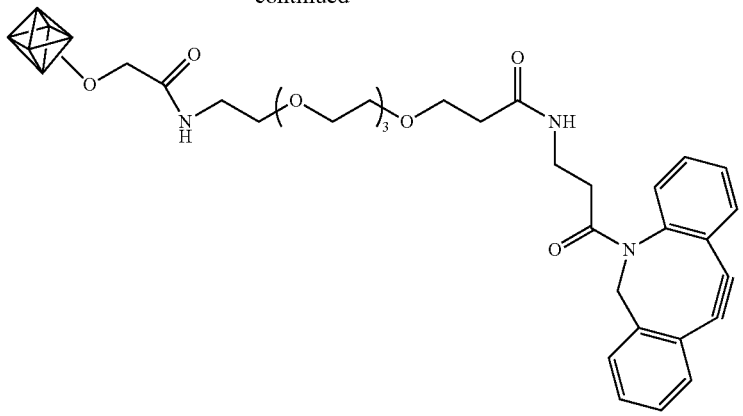

As shown in Scheme 4, the nanodiamond acyl chloride of example 2 is suspended in dichloromethane and the acyl groups are amidated by addition of amine-PEG4-DBCO, triethyl amine, and the catalyst 4-(dimethylamino)pyridine (DMAP) to the suspension.

In particular, the dry acyl chloride-functionalized nanodiamonds (16 mg) are suspended in 1 mL of dichloromethane (DCM) (Sigma-Aldrich). To this, amine-PEG4-DBCO (2 mg) (Click Chemistry Tools), triethylamine (100 μL), and 4-(dimethylamino)pyridine (DMAP, 5 mg) are added. The diamond dispersion is kept at 39° C. for one day. The diamonds are then isolated by centrifugation and thoroughly washed with DCM and methanol in order to remove unreacted reagents. The diamonds are dried under vacuum.

Example 9. Coupling Acid Chloride-Enriched Nanodiamonds with HALOTAG® Amine (O2) Ligand Experiments are performed to functionalize the carboxylic acid-enriched detonation nanodiamonds made by the method of Example 2 with commercially available HALOTAG® amine (O2) ligand (Promega Corporation).

The functionalization is shown schematically in Scheme 5.

As shown in Scheme 5, the nanodiamond acyl chloride of example 2 is suspended in dichloromethane and the acyl groups are amidated by addition of HALOTAG® amine ligand, triethyl amine, and the catalyst 4-(dimethylamino)pyridine (DMAP) to the suspension.

In particular, the dry acyl chloride-functionalized nanodiamonds (16 mg) are suspended in 1 mL of dichloromethane (DCM) (Sigma-Aldrich). To this, triethylamine (100 μL), HALOTAG® amine ligand (Promega Corporation, 2 mg) and 4-(dimethylamino)pyridine (DMAP, 5 mg) are added. The diamond dispersion is kept at 39° C. for one day. The diamonds are then isolated by centrifugation and thoroughly washed with DCM and methanol in order to remove unreacted reagents. The diamonds are dried under vacuum.

Example 10. Coupling Acid Chloride-Enriched Nanodiamonds with Amine-SNAP-TAG® Ligand Experiments are performed to functionalize the carboxylic acid-enriched detonation nanodiamonds made by the method of Example 2 with O⁶-alkyl guanine, a substrate for commercially available SNAP-TAG® (New England Biolabs, Inc.

Scheme 5.

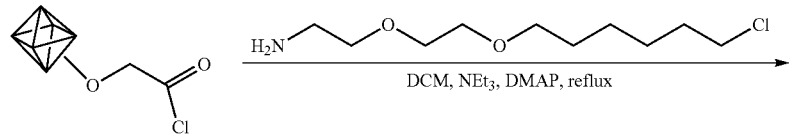

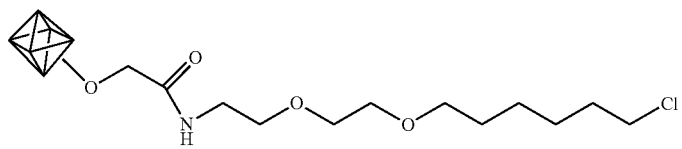

The functionalization is shown schematically in Scheme 6.

for commercially available CLIP-TAG™ (New England Biolabs, Inc.). The functionalization is shown schematically in Scheme 7.

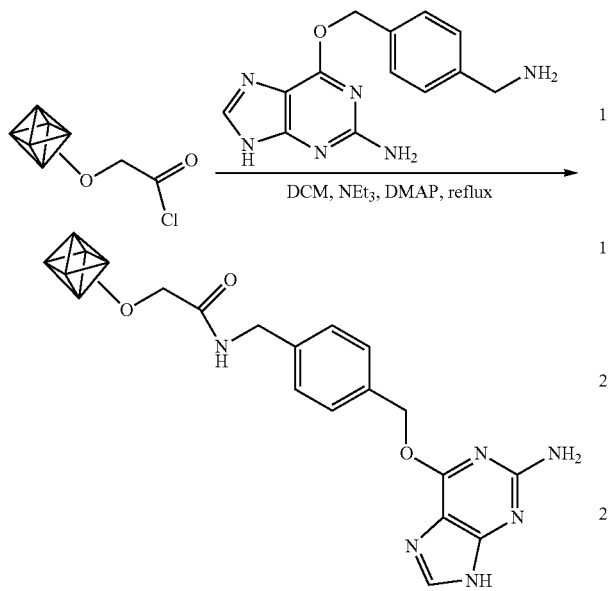

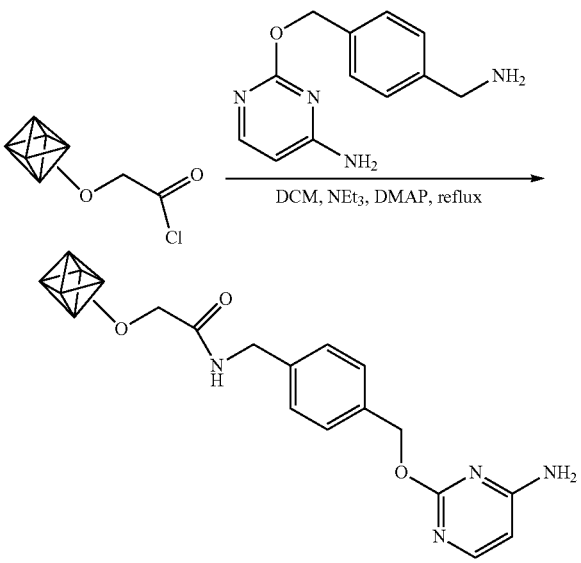

As shown in Scheme 6, the nanodiamond acyl chloride of example 2 are suspended in dichloromethane and the acyl groups are amidated by addition of 4-aminomethyl-benzyl-6'-oxyguanine (O$^6$-alkyl guanine), triethylamine, and the catalyst 4-(dimethylamino)pyridine (DMAP) to the suspension.

In particular, the dry acyl chloride-functionalized nanodiamonds (16 mg) are suspended in 1 mL of dichloromethane (DCM) (Sigma-Aldrich). To this, aminomethlbenzyl-6'-oxyguanine (O$^6$-alkylguanine aminomethyl) (New England Biolabs, 2 mg), triethylamine (100 µL), and 4-(dimethylamino)pyridine (DMAP, 5 mg) are added. The diamond dispersion is kept at 39° C. for one day. The diamonds are then isolated by centrifugation and thoroughly washed with DCM and methanol in order to remove unreacted reagents. The diamonds are dried under vacuum.

Example 11. Coupling Acid Chloride-Enriched Nanodiamonds with CLIP-TAG™ Ligand Experiments are performed to functionalize the carboxylic acid-enriched detonation nanodiamonds made by the method of Example 2 with O$^2$-benzylcytosine, a substrate As shown in Scheme 7, the nanodiamond acyl chloride of example 2 are suspended in dichloromethane and the acyl groups are amidated by addition of 4-aminomethyl-benzyl-2-oxycytosine (O$^2$-benzyl cytosine aminomethyl), triethyl amine, and the catalyst 4-(dimethylamino)pyridine (DMAP) to the suspension.

In particular, the dry acyl chloride-functionalized nanodiamonds (16 mg) are suspended in 1 mL of dichloromethane (DCM) (Sigma-Aldrich). To this, 4-aminomethyl-benzyl-2'-oxyguanine (O$^2$-benzyl cytosine aminomethyl, 2 mg) (New England Biolabs, Inc.), triethylamine (100 µL), and 4-(dimethylamino)pyridine (DMAP, 5 mg) are added. The diamond dispersion is kept at 39° C. for one day. The diamonds are then isolated by centrifugation and thoroughly washed with DCM and methanol in order to remove unreacted reagents. The diamonds are dried under vacuum.

Example 12. General Procedure for Coupling Acid Chloride-Enriched Nanodiamonds with Amine-Linked-Tags The procedure of example 7 with the amines below produced the following compounds.

1.

Aminoethyl-PEG4-maleimide

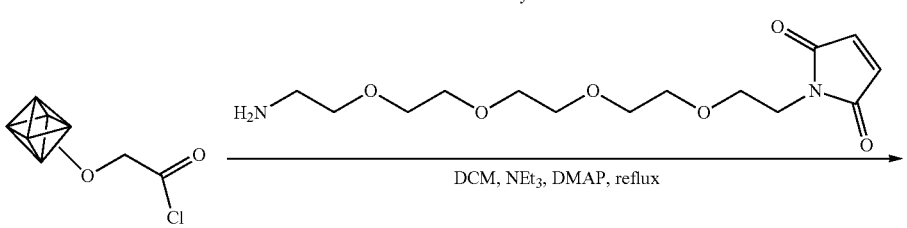

-continued

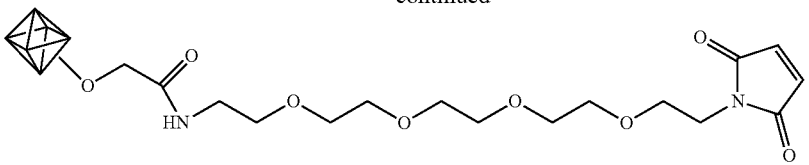

Aminoethyl-PEG4-acetyl chloride

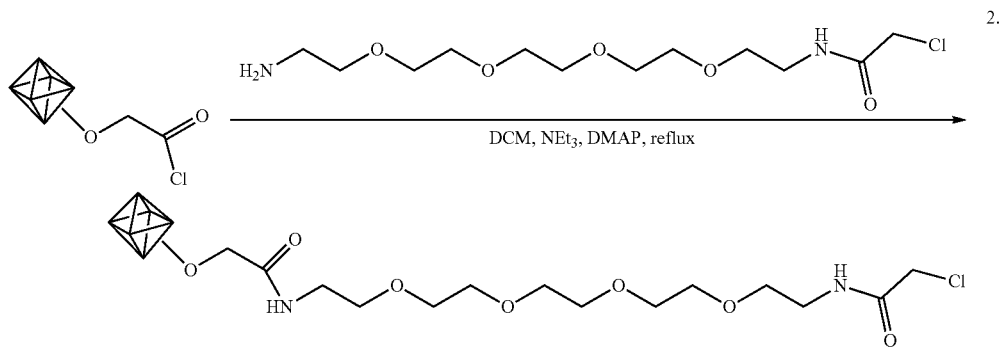

Aminoethyl-PEG4-acetyl thiolacetyl

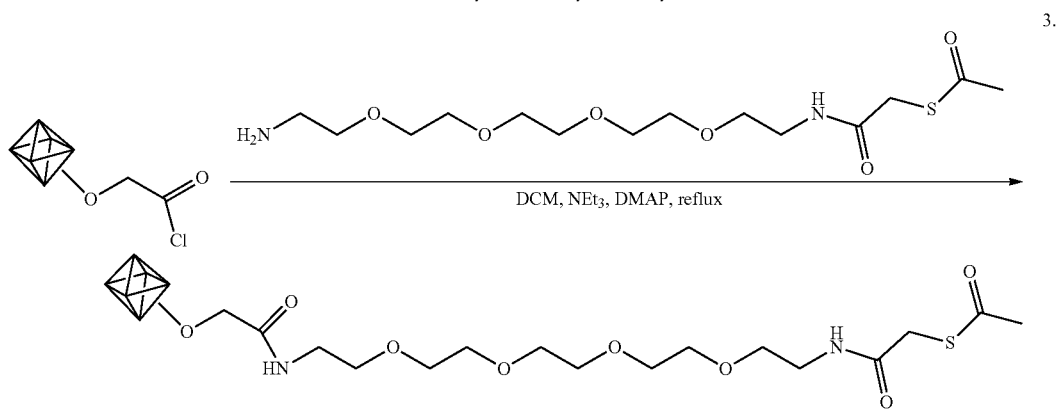

In summary, methods to generate carboxylic acids selectively from the wide variety of oxygen-containing functional groups present on the surface of a carbon nanoparticle after acid oxidation and surface-functionalized carbon nanoparticles made by the methods have been shown. The method results in greatly enriched levels of surface carboxylic acids on the carbon nanoparticles which can be efficiently derivatized to alternative functional groups. The method can be applied to a broad range of carbon nanoparticles. The surface-functionalized carbon nanoparticles are shown to have increased levels of functional groups per mass of nanoparticle.

The invention is further illustrated by the following Embodiments, which are not intended to be limiting.

Embodiment 1

A method of increasing a density of carboxylic acids on a surface of a carbon nanoparticle, the method comprising contacting an oxygen-containing functional group on a surface of a carbon nanoparticle with a reducing agent to provide a hydroxyl group; reacting the hydroxyl group with a diazoacetate ester in the presence of a transition metal catalyst to provide an ester, the diazoacetate ester having the structure $$\begin{array}{c} \text{H} \\ \underset{N_2}{\overset{O}{\parallel}} \\ \text{OR,} \end{array}$$

wherein R is a C1-8 hydrocarbyl, preferably tert-butyl, methyl, ethyl, isopropyl, allyl, benzyl, pentafluorophenyl, or N-succinimidyl; and cleaving the ester to provide a carboxylic acid group

Embodiment 2

The method of claim 1, wherein the reducing agent is a metal hydride.

Embodiment 3

The method of embodiment 2, wherein the metal hydride is lithium triethylborohydride (LiBHEt$_3$), LiAlH$_4$, AlH$_3$, Al(BH$_4$)$_3$ (NaBH$_4$+AlCl$_3$), LiBH$_4$, Mg(BH$_4$)$_2$ (NaBH$_4$+MgCl$_2$), Ca(BH$_4$)$_2$ (NaBH$_4$+CaCl$_2$), Na/NH$_3$, Li/NH$_3$, Ca/NH$_3$, or a combination thereof.

Embodiment 4

The method of any one of embodiments 1 to 3, wherein the carbon nanoparticle is a carbon nanotube, a fullerene, a graphene, graphene oxide, a nanodiamond, or a combination thereof.

Embodiment 5

The method of any one of embodiments 1 to 4, wherein the carbon nanoparticle is a nanodiamond.

Embodiment 6

The method of embodiment 5, wherein the nanodiamond is a detonation diamond, a fluorescent nanodiamond, or a combination thereof.

Embodiment 7

The method of any one of embodiments 1 to 6, wherein the transition metal catalyst is $Rh_2(OAc)_4$, $Rh_2(NHAc)_4$, $Rh_2(NHCOCF_3)_4$, $Rh_2(NHCOC_3F_7)_4$, $Cu(Otf)_2$, $CuI.P(OMe)_3$, $Ni(acac)_2$, $BF_3.Et_2O$, or a combination thereof.

Embodiment 8

The method of any one of embodiments 1 to 7, wherein the transition metal catalyst is $Rh_2(OAc)_4$, $Rh_2(NHAc)_4$, or a combination thereof.

Embodiment 9

The method of any one of embodiments 1 to 8, wherein R is tert-butyl, methyl, ethyl, isopropyl, allyl, benzyl, pentafluorophenyl, or N-succinimidyl.

Embodiment 10

The method of any one of embodiments 1 to 9, further comprising: functionalizing the carboxylic acid group to a second functional group.

Embodiment 11

The method of embodiment 10, wherein the second functional group is an acyl chloride, an amide, a pegylate, a biotinylate, a folate, a thiol, a maleimide, an active ester, an amine, a chelated gadolinium, an azide, an alkyne, a protein tag ligand, or a dendrimer linkage.

Embodiment 12

The method of embodiment 10 or 11, wherein functionalizing the carboxylic acid group comprises converting the carboxylic acid group to an acyl chloride.

Embodiment 13

The method of any one of embodiments 1-12, further comprising oxidizing the surface of the carbon nanoparticle, preferably with an oxidizing acid mixture.

Embodiment 14

A surface-functionalized carbon nanoparticle comprising a first functional group attached to a surface of the carbon nanoparticle, wherein the first functional group is present in an amount of at least $1 \times 10^{17}$ first functional group/g of carbon nanoparticle, at least 100 first functional group/carbon nanoparticle, or at least 1 first functional group/210 $nm^2$ of the surface; preferably at least $3 \times 10^{17}$ first functional group/g of carbon nanoparticle, at least 300 first functional group/carbon nanoparticle, or at least 1 first functional group/70 $nm^2$ of the surface.

Embodiment 15

The carbon nanoparticle of embodiment 14, which is a carbon nanotube, a fullerene, graphene, graphene oxide, a nanodiamond, or a combination thereof.

Embodiment 16

The carbon nanoparticle of embodiment 14 or 15 which is a nanodiamond.

Embodiment 17

The carbon nanoparticle of embodiment 16, wherein the nanodiamond is a detonation diamond, a fluorescent nanodiamond, or a combination thereof.

Embodiment 18

The carbon nanoparticle of any one of embodiments 14 to 17, wherein the first functional group is a carboxylic acid.

Embodiment 19

The carbon nanoparticle of any one of embodiments 14 to 18, wherein the carboxylic acid group is further functionalized to a second functional group.

Embodiment 20

The carbon nanoparticle of embodiment 19, wherein the second functional group is an acyl chloride, an amide, a pegylate, a biotinylate, a folate, a thiol, a maleimide, an active ester, an amine, a chelated gadolinium, an azide, an alkyne, a protein tag ligand, or a dendrimer linkage.

Embodiment 21

The carbon nanoparticle of any one of embodiments 14 to 17, wherein the first functional group is an acyl chloride, an amide, a pegylate, a biotinylate, or an amine.

Embodiment 22

The carbon nanoparticle of any one of embodiments 14 to 21, comprising an alkyne covalently coupled to the surface of the carbon nanoparticle, optionally the alkyne is coupled via a linker.

Embodiment 23

The carbon nanoparticle of any one of embodiments 14 to 21, comprising a dibenzocyclooctyne covalently coupled to the surface of the carbon nanoparticle, optionally the dibenzocyclooctyne is coupled via a linker.

Embodiment 24

The carbon nanoparticle of any one of embodiments 14 to 21, comprising an alkylating group covalently coupled to the surface of the carbon nanoparticle, optionally the alkylating group is coupled via a linker.

Embodiment 25

The carbon nanoparticle of any one of embodiments 14 to 21, comprising a protected thiol covalently coupled to the surface of the carbon nanoparticle, optionally the protected thiol is coupled via a linker.

Embodiment 26

The carbon nanoparticle of any one of embodiments 14 to 21, comprising a protein tag system ligand covalently coupled to the surface of the carbon nanoparticle, optionally the protein tag system ligand is coupled via a linker.

Embodiment 27

The carbon nanoparticle of embodiment 26, wherein the protein tag system ligand comprises a haloalkane.

Embodiment 28

The carbon nanoparticle of embodiment 26, wherein the protein tag system ligand comprises an $O^6$-alkylguanine.

Embodiment 29

The carbon nanoparticle of embodiment 26, wherein the protein tag system ligand comprises an $O^2$-benzylcytosine.

Embodiment 30

The carbon nanoparticle of any one of embodiments 22 to 29, wherein the linker comprises a polyethylene glycol.

Embodiment 31

The carbon nanoparticle of any one of embodiments 14 to 30, wherein the nanoparticle is a nanodiamond.

Embodiment 32

The method of embodiment 10, wherein functionalizing the carboxylic acid group comprises covalently coupling an alkyne to the carboxylic acid group, optionally wherein the alkyne is coupled via a linker.

Embodiment 33

The method of embodiment 10, wherein functionalizing the carboxylic acid group comprises covalently coupling a dibenzocyclooctyne to the carboxylic acid group, optionally wherein the dibenzocyclooctyne is coupled via a linker.

Embodiment 34

The method of embodiment 10, wherein functionalizing the carboxylic acid group comprises covalently coupling an alkylating group to the carboxylic acid group, optionally wherein the alkylating group is coupled via a linker.

Embodiment 35

The method of embodiment 10, wherein functionalizing the carboxylic acid group comprises covalently coupling a protected thiol to the carboxylic acid group, optionally wherein the protected thiol is coupled via a linker.

Embodiment 36

The method of embodiment 10, wherein functionalizing the carboxylic acid group comprises covalently coupling a protein tag system ligand to the carboxylic acid group, optionally wherein the protein tag system ligand is coupled via a linker.

Embodiment 37

The method of embodiment 36, wherein the protein tag system ligand comprises a haloalkane.

Embodiment 38

The method of embodiment 36, wherein the protein tag system ligand comprises an $O^6$-alkylguanine.

Embodiment 39

The method of embodiment 36, wherein the protein tag system ligand comprises an $O^2$-benzylcytosine.

Embodiment 40

The method of any one of embodiments 32 to 39, wherein the linker comprises a polyethylene glycol.

Embodiment 41

The method any one of embodiments 10, 32 to 40, wherein the nanoparticle is a nanodiamond.

The compositions, methods, and articles can alternatively comprise, consist of, or consist essentially of, any appropriate components or steps herein disclosed. The compositions, methods, and articles can additionally, or alternatively, be provided so as to be devoid, or substantially free, of any steps, components, materials, ingredients, adjuvants, or species that are otherwise not necessary to the achievement of the function and/or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements can be combined in any suitable manner in the various embodiments.

Unless defined otherwise, technical and scientific terms used herein have the same meaning as is commonly understood by one of skill in the art to which this invention belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen can arise to applicants or others skilled in the art. Accordingly, the appended claims as filed and as they may be amended are intended to embrace all such alternatives, modifications variations, improvements, and substantial equivalents.

What is claimed is:

1. A method of increasing a density of carboxylic acids on a surface of a carbon nanoparticle, the method comprising
contacting an oxygen-containing functional group on a surface of a carbon nanoparticle with a reducing agent to provide a hydroxyl group;
reacting the hydroxyl group with a diazoacetate ester in the presence of a transition metal catalyst to provide an ester coupled to the carbon nanoparticle by an ether linkage, the diazoacetate ester having the structure

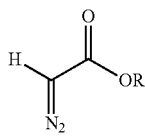

wherein R is a $C_{1-8}$ hydrocarbyl; and
cleaving the ester to provide a carboxylic acid group.

2. The method of claim 1, wherein the reducing agent is a metal hydride.

3. The method of claim 1, wherein the carbon nanoparticle is a carbon nanotube, a fullerene, a graphene, graphene oxide, a nanodiamond, or a combination thereof.

4. The method of claim 1, wherein R is tert-butyl, methyl, ethyl, isopropyl, allyl, benzyl, pentafluorophenyl, or N-succinimidyl.

5. The method of claim 1, further comprising
oxidizing the surface of the carbon nanoparticle.

6. The method of claim 1, wherein the transition metal catalyst is $Rh_2(OAc)_4$, $Rh_2(NHAc)_4$, $Rh_2(NHCOCF_3)_4$, $Rh_2(NHCOC_3F_7)_4$, $Cu(Otf)_2$, $CuI.P(OMe)_3$, $Ni(acac)_2$, $BF_3$-$Et_2O$, or a combination thereof.

7. The method of claim 6, wherein the transition metal catalyst is $Rh_2(OAc)_4$, $Rh_2(NHAc)_4$, or a combination thereof.

8. The method of claim 1, further comprising:
functionalizing the carboxylic acid group to a second functional group.

9. The method of claim 8, wherein the second functional group is an acyl chloride, an amide, a pegylate, a biotinylate, a folate, a thiol, a maleimide, an active ester, an amine, a chelated gadolinium, an azide, an alkyne, a protein tag ligand, or a dendrimer linkage.

10. The method of claim 8, wherein functionalizing the carboxylic acid group comprises
covalently coupling the second functional group to the carboxylic acid group, optionally wherein the second functional group is coupled via a linker, wherein the second functional group is an alkyne, a dibenzocyclooctyne, an alkylating group, a protected thiol, or a protein tag system ligand.

11. A surface-functionalized carbon nanoparticle comprising
a first functional group attached to a surface of the carbon nanoparticle by an ether linkage,
wherein the first functional group is present in an amount of at least $1 \times 10^{17}$ first functional group/g of carbon nanoparticle, at least 100 first functional group/carbon nanoparticle, or at least 1 first functional group/210 $nm^2$ of the surface.

12. The carbon nanoparticle of claim 11, which is a carbon nanotube, a fullerene, graphene, graphene oxide, a nanodiamond, or a combination thereof.

13. The carbon nanoparticle of claim 11, wherein the first functional group is an acyl chloride, an amide, a pegylate, a biotinylate, or an amine.

14. The carbon nanoparticle of claim 11, comprising
an alkyne covalently coupled to the surface of the carbon nanoparticle, optionally the alkyne is coupled via a linker; or
a dibenzocyclooctyne covalently coupled to the surface of the carbon nanoparticle, optionally the dibenzocyclooctyne is coupled via a linker.

15. The carbon nanoparticle of claim 11, comprising
an alkylating group covalently coupled to the surface of the carbon nanoparticle, optionally the alkylating group is coupled via a linker; or
a protected thiol covalently coupled to the surface of the carbon nanoparticle, optionally the protected thiol is coupled via a linker.

16. The carbon nanoparticle of claim 11, comprising a protein tag system ligand covalently coupled to the surface of the carbon nanoparticle, optionally the protein tag system ligand is coupled via a linker.

17. The carbon nanoparticle of claim 16, wherein the protein tag system ligand comprises a haloalkane, an $O^6$-alkylguanine, or an $O^2$-benzylcytosine.

18. The carbon nanoparticle of claim 11, wherein the first functional group is a carboxylic acid.

19. The carbon nanoparticle of claim 18, wherein the carboxylic acid group is further functionalized to a second functional group.

20. The carbon nanoparticle of claim 19, wherein the second functional group is an acyl chloride, an amide, a pegylate, a biotinylate, a folate, a thiol, a maleimide, an active ester, an amine, a chelated gadolinium, an azide, an alkyne, a protein tag ligand, or a dendrimer linkage.

* * * * *